(12) United States Patent　　(10) Patent No.:　　US 7,556,375 B2
　　Caroline et al.　　　　　　　　(45) Date of Patent:　　Jul. 7, 2009

(54) SOFT LENS ORTHOKERATOLOGY

(75) Inventors: Patrick Joseph Caroline, Lake Oswego, OR (US); Peter Donald Bergenske, Hillsboro, OR (US); Jennifer Denise Choo, Burnaby (CA); Stacy Sanaz Aboutalebi, Pleasant Hill, CA (US); Simon Rodney Evans, Botany (AU); Arthur Ho, Clovelly (AU); Eric Basil Papaspiliotopoulos, Paddington (AU); Brien Anthony Holden, Kingsford (AU)

(73) Assignee: The Institute for Eye Research, Sydney, New South Wales (AU)

( * ) Notice: Subject to any disclaimer, the term of this patent is extended or adjusted under 35 U.S.C. 154(b) by 0 days.

(21) Appl. No.: 10/551,884

(22) PCT Filed: Aug. 27, 2004

(86) PCT No.: PCT/AU2004/001156

§ 371 (c)(1),
(2), (4) Date: Feb. 6, 2007

(87) PCT Pub. No.: WO2005/022242

PCT Pub. Date: Mar. 10, 2005

(65) Prior Publication Data

US 2007/0216859 A1　　Sep. 20, 2007

Related U.S. Application Data

(60) Provisional application No. 60/498,423, filed on Aug. 27, 2003.

(51) Int. Cl.
　　G02C 7/04　　(2006.01)
(52) U.S. Cl. .............................. 351/160 H; 351/160 R; 351/161
(58) Field of Classification Search ............. 351/160 R, 351/160 H, 161–162
See application file for complete search history.

(56) References Cited

U.S. PATENT DOCUMENTS

| 3,482,906 | A | | 12/1969 | Volk |
| 4,952,045 | A | | 8/1990 | Stoyan |
| 5,428,412 | A | | 6/1995 | Stoyan |
| 6,010,219 | A | * | 1/2000 | Stoyan ................... 351/160 R |
| 6,241,355 | B1 | | 6/2001 | Barsky |
| 2002/0101563 | A1 | | 8/2002 | Miyamura et al. |
| 2002/0163620 | A1 | | 11/2002 | Miyamura et al. |
| 2003/0095232 | A1 | * | 5/2003 | Mitsui ........................ 351/176 |

FOREIGN PATENT DOCUMENTS

| CN | 1420380 | 5/2003 |
| GB | 2 382 155 A | 5/2003 |
| WO | WO 96/31545 | 10/1996 |
| WO | WO 02/29446 A2 | 4/2002 |
| WO | WO 02/41070 A1 | 5/2002 |

OTHER PUBLICATIONS

State Intellectual Property Office of People's Republic of China, First Office Action for Application No. 200480005257.0; mailing date, Feb. 22, 2008, 5 pages.

(Continued)

*Primary Examiner*—Ricky L Mack
*Assistant Examiner*—James R Greece
(74) *Attorney, Agent, or Firm*—Blakely Sokoloff, Taylor & Zafman LLP

(57) ABSTRACT

A corneal reshaping by means of a soft contact lens to manipulate tear pressure gradient to produce a dimensional change to the surface profile of the cornea of the wearer to provide at least a temporary change in the refractive state of the eye eliminating the need for other refractive corrections. The contact lens has mechanical properties and/or a geometric shape such that when the lens is fitted to the eye the pressure applied to the eye via the lens will vary in a radial direction between at least one zone of higher pressure and at least one zone of lower pressure so that wearing the lens will over time cause a dimensional change to the surface layer of the cornea.

13 Claims, 40 Drawing Sheets

OTHER PUBLICATIONS

Belytschkio, Liu, and Moran, "Nonlinear Finite Elements for Continua and Structures," Table of Contents, Wiley (2001).

Brien A. Holden and George W. Mertz, "Critical Oxygen Levels to Avoid Corneal Edema for Daily and Extended Wear Contact Lenses," Investigative Ophthalmology.& Visual Science, pp. 1161-1167 (Oct. 1984).

C.R. Munnerlyn, S.J. Koons, and J. Marshall, "Photorefractive Keratectomy: A Technique to Laser Refractive Surgery," J. Cataract Refractive Surgery, pp. 46-52 (1988).

Helen A. Swarbrick, "Orthokeratology Review and Update (Invited Review)," Clinical and Experimental 89.3, pp. 124-143 (May 2006).

"Rigid Gas Permeable," http://www.leisvision.com/leis/rigidgaspermeable.html, 2 pgs (Mar. 3, 2008).

* cited by examiner

SOFT LENS ORTHOKERATOLOGY

CROSS-REFERENCE TO OTHER APPLICATIONS

This is a National Phase of International Application No. PCT/AU2004/001156, filed on Aug. 27, 2004, which claims priority from U.S. Provisional Patent Application No. 60/498,423, filed on Aug. 27, 2003.

FIELD OF THE INVENTION

This invention relates generally to contact lenses, and more particularly, to lenses suitable for corneal reshaping to correct, decrease or prevent refractive error.

BACKGROUND OF THE INVENTION

The human visual system consists of three primary components, the cornea, the crystalline lens and the retina. Emmetropia is the condition in which incoming parallel light rays focus perfectly on to the retina so that clear images i.e. 20/20 vision, will be seen. In myopia, or nearsightedness, parallel light rays are focused anterior to the retina resulting in a blurred retinal image. In hyperopia or farsightedness, the parallel light rays focus posterior to the retina again resulting in an out of focus image. Other refractive anomalies such as astigmatism and presbyopia also result in blurred retinal images.

Corrective modalities for the above mentioned refractive errors include spectacles, contact lenses and refractive surgery. Spectacle lenses have been the traditional mode used to correct refractive errors and they consist of concave, convex or cylindrical lenses to bring the unfocussed parallel rays of light to focus on the retina. Contact lenses accomplish a similar optical correction by the placement of a rigid or soft plastic material directly onto the surface of the cornea. Surgical correction of refractive errors (i.e. RK, PRK, LASIK, intraocular lenses) works by either remodeling the surface of the cornea or by addition of a corrective lens surgically implanted within the eye. In 1962, Jessen introduced a non-surgical contact lens technique for remodeling the corneal surface which was eventually referred to as orthokeratology.

Traditionally, orthokeratology has been defined as the temporary reduction or elimination of refractive errors (myopia, hyperopia, astigmatism and presbyopia) through the application of specially designed rigid gas permeable lenses (RGPs) to reshape the anterior surface of the cornea. The desired topographical changes (central corneal flattening to correct myopia and central corneal steepening to correct hyperopia) are made possible through a unique posterior lens geometry in which the center of the lens incorporates a different radius of curvature than the mid-periphery. One such geometry that is commonly employed is referred to as a "reverse geometry design". In contemporary orthokeratology, the posterior lens configuration reshapes the corneal surface overnight while the patient is sleeping. Upon awakening, the lenses are removed and the patient experiences reduced refractive error and improved vision without glasses, contact lenses, or refractive surgery. Since the corneal remodeling is not permanent, it is necessary for the patient to wear the rigid contact lenses every night or every other night to retain the desired effect.

All previous orthokeratology technologies have used hard lenses or RGP lenses to achieve the corneal reshaping effects.

While research is continuing into the mechanism underlying RGP orthokeratology, current understanding is that a hydraulic, tissue-altering force is generated beneath a rigid lens in which a significant differential in tear volume may be present.

In the case of myopic orthokeratology, the desired central flattening effect is made possible through an RGP lens that incorporates a central radius of curvature that is flatter (ie larger radius of curvature) than the curve of the central cornea. In the mid-periphery, the lens incorporates a radius of curvature that is steeper (ie small radius of curvature) than the curve of the cornea. Together, these curves combine to form the basis of a reverse geometry lens design.

The posterior shape of a reverse geometry lens creates a positive "push" force on the center of the cornea by virtue of a thin (approximately 5 micron) tear layer across the central cornea. The steeper mid-peripheral curve of the lens creates a thick tear layer (approximately 550 microns) resulting in a negative pressure or "pull" force. This negative pressure leads at least in part to a relative increase in mid-peripheral corneal thickness with respect to central thickness. Together, these two forces create the desired changes seen in myopic orthokeratology.

In the case of hyperopic orthokeratology, the current understanding is that the mechanism works opposite to that of myopic orthokeratology. In other words, the lens design creates a "pull" (negative) pressure in the center and a "push" (positive) pressure in the mid-periphery. These forces may be generated by a reverse geometry lens design that incorporates both a steep central radius of curvature and a flat mid-peripheral radius of curvature. This configuration creates the desired changes seen in hyperopic orthokeratology.

Currently, there is a wide range of lens designs marketed for corneal reshaping (Table 1). In the United States, at least one design, the Paragon CRT, has been FDA approved for overnight corneal reshaping. The remaining lens designs are either approved for daily wear only or currently in some phase of their clinical studies for overnight FDA approval. All of the lenses in Table 1 are RGP lenses.

TABLE 1

A number of lens designs marketed for corneal reshaping.

| Lens Design | Manufacturer |
| --- | --- |
| Corneal Refractive Therapy | Paragon Vision Sciences |
| BE Design | Precision Technology |
| Contex E System | Contex |
| DreimLens | ReimLens Inc. |
| Emerald Design | Euclid Systems |
| NightForm | Correctech |
| Controlled Kerato Reformation | Sami El Hage |
| R&R Design | Rinehart/Reeves |
| NightMove | Roger Tabb |
| Fargo Design | Jim Day |
| OrthoFocus | Metro Optics |
| Wave System | Custom Craft |
| Reversible Corneal Therapy | ABBA Optical |
| Free Dimension/e Lens | E and E Optics |
| Alignment Series/Falcon | G.P. Specialist |

The Paragon CRT lens consists of three primary zones. The first zone consists of a central base curve radius designed to correct myopic refractive error. This flatter radius of curvature is instrumental in creating the appropriate forces beneath the lens to facilitate the remodeling of corneal tissue. The second zone, the return zone, is a sigmoid shaped curve that controls the amount of lens clearance across the central cornea. A shallower sigmoid curve brings the base curve into closer apposition to the cornea, whereas a deeper sigmoid curve results in greater apical clearance. The third and final zone provides alignment of the lens across the mid-peripheral cornea. This zone terminates in a controlled edge curve designed to maximize patient comfort.

For many years, RGP lenses were the physiologically preferred lenses for most contact lens wearers. This was because RGP lenses have high levels of oxygen transmissibility, and are generally considered to be relatively physiologically non-damaging to the wearer's eye, for example through the greater tear exchange achievable. RGP lenses are not, however, particularly comfortable to wear, and more recently soft contact lenses have become the lens of choice for most patients. Indeed, in some countries, approximately 90% of contact lens wearers now use soft lenses. Silicone hydrogel lenses are a relatively recent development, and provide high levels of oxygen transmissibility thereby eliminating the previous disadvantage of soft contact lenses and permitting safe overnight wear while retaining a high comfort level. Most recently, silicone hydrogel extended or continuous wear lenses have been developed which have sufficient tear and oxygen transmissibility so as not to cause damage to the eye, even when the lenses are worn overnight during sleep, or even continuously for up to 30 days.

It will be appreciated that soft lenses tend to conform far better to the shape of the wearer's eyes than do RGP lenses. Indeed, it is the softness and conformability of soft lenses that is believed to provide high comfort levels for the wearer. The orthokeratology process requires some reshaping of the surface of the eye, and accordingly it has been accepted wisdom that soft lenses, because of the high degree of conformity to the surface of the eye, would be unsuitable for orthokeratology.

SUMMARY OF THE INVENTION

According to a first aspect of the invention there is provided a soft contact lens having a posterior surface for fitting to the eye of a wearer, and a convex anterior surface, the contact lens having mechanical properties and/or a geometric shape such that when the lens is fitted to the eye the pressure applied to the eye by or via the lens will vary in a radial direction between at least one zone of higher pressure and at least one zone of lower pressure, the pressure gradient between said zones, and the location of said zones, being selected so as to cause a dimensional change to the surface layer of the cornea of the eye to thereby at least temporarily cause the refractive state of the eye to change.

Preferably the posterior surface of said contact lens has a shape that differs from the contour of the eye such that some annular portion of the lens at a particular radial distance from the center of the lens will be closer to the surface of the eye than another annular portion of the lens at a different radial distance from the center of the lens.

Preferably the pressures applied to the eye at each annular portion are such as to define a pressure gradient which is sufficiently steep that corneal thickness, and primarily epithelial thickness, will tend to be less near or within the zone of higher pressure and greater near or within the zone of lower pressure.

The lens may be constructed so as to have a natural or normal (non-everted) orientation and an everted (inside out) orientation, the lens being stable in both orientations, and wherein, the posterior surface of the everted lens is defined by the anterior surface of the non-everted lens.

The invention extends to a method of refractive error reduction of an eye by corneal reshaping including the steps of:

determining the required refractive correction for the eye; and selecting a soft lens formed of a material and having a geometric configuration such that when fitted to the eye will apply pressures to the surface of the eye in such manner as to assist in the required corneal reshaping.

It would be appreciated that the present method may be augmented by adding the step of mapping the surface shape, e.g. by corneal topography, of at least that part of the eye which is to be subjected to reshaping in order to improve the predictability of the corneal reshaping. However, it is envisaged that for high-volume production contact lenses which aims to achieve the outcome in an average individual of a large population, corneal mapping is not absolutely essential.

The invention will now be discussed in more detail with reference to the attached drawings. The description and drawings are not however, intended to limit the broad subject of the invention as defined in the claims.

DETAILED DESCRIPTION OF PREFERRED EMBODIMENTS

Figure 1:
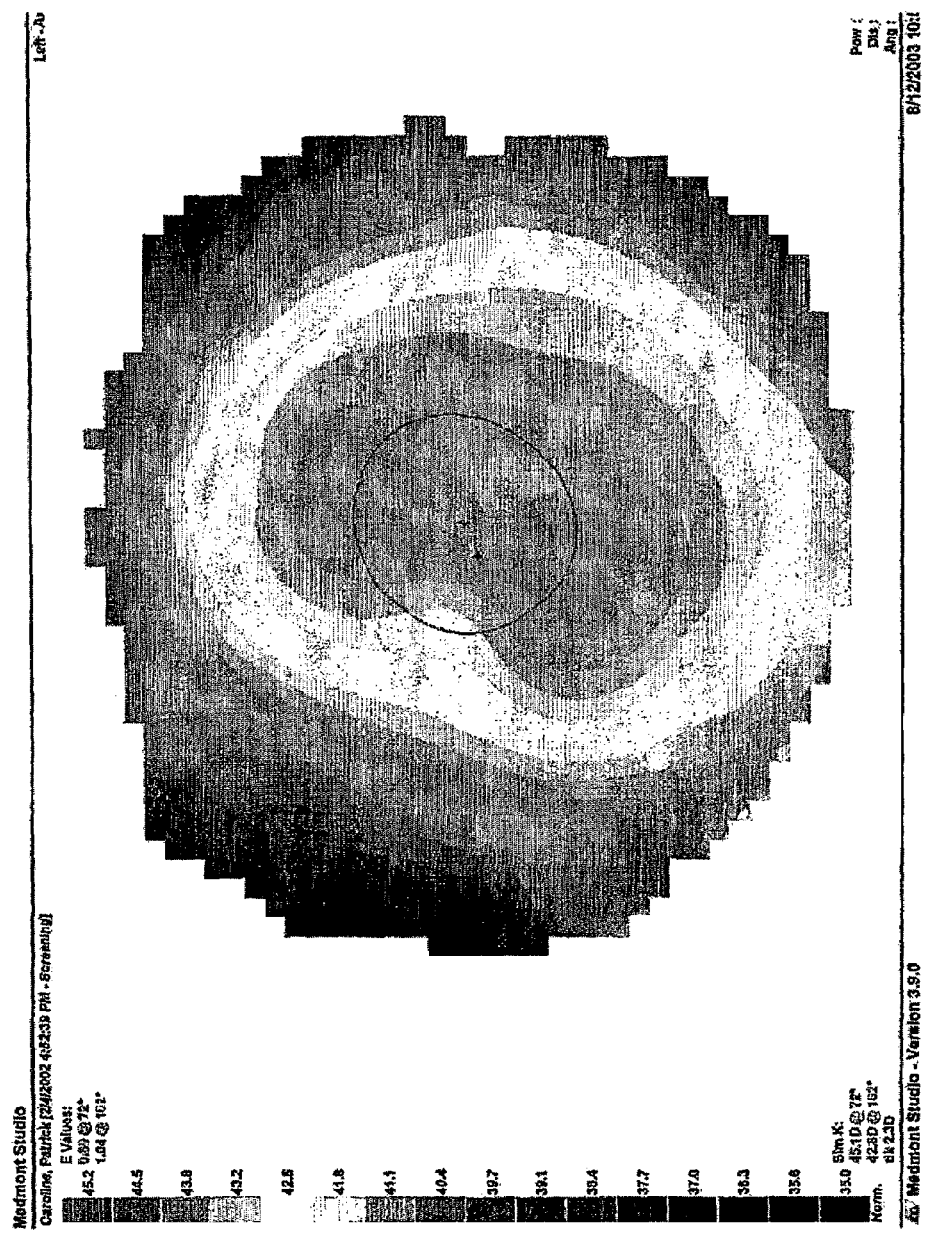
FIGS. 1 to 26 show different corneal topography maps for eyes of subjects who received orthokeratology treatment in accordance with the invention.

The human epithelium is approximately 50 microns thick. The amount of tissue compression or displacement, that is, reduction in tissue thickness, can be estimated using the Munnerlyn Formula commonly incorporated into today's excimer lasers used for corneal photo-refractive surgery (Munnerlyn C. R., Koons S. J., Marshall J., *Photorefractive Keratectomy: A Technique for Laser Refractive Surgery*, J. CATARACT REFRACT. SURG. 1988 14:46-52). This formula can be used to estimate the amount of tissue manipulation required for a desired refractive change.

Tissue Thickness Reduction=((Optical Zone Diameter)$^2$×Refractive Error)/3

The Munnerlyn Formula assumes that the posterior surface of the cornea remains fixed.

EXAMPLE

Treatment zone diameter=5.0 mm

OZD squared (5.0×5.0)=25 mm$^2$ x target refractive error (−2.50 D)=−62.50 microns / 3=−20.83 microns Required Tissue Thickness Change=−21 microns In the context of corneal reshaping the change in corneal sagittal depth over the treatment zone for a −2.5 D correction is approximately 20 microns. Table 2 describes how the effective refractive change can increase as the treatment zone decreases.

TABLE 2

Relationship between treatment zone diameter and refractive change.

| Treatment Zone Diameter | Treatment Depth | Expected Rx Change |
| --- | --- | --- |
| 6.0 mm | 20 microns | −1.75 D |
| 5.0 mm | 20 microns | −2.50 D |
| 5.0 mm | 20 microns | −2.50 D |
| 4.0 mm | 20 microns | −3.75 D |
| 3.0 mm | 20 microns | −6.75 D |

When the Munnerlyn Formula is applied to contact lens corneal reshaping, the results demonstrate that minimal tissue displacement (approximately 9 microns per diopter) is required to achieve the desired optical result. The formula also helps to clarify the relationship between treatment zone diameter and the amount of tissue displaced (Table 3).

TABLE 3

Corneal tissue displacement required for −3.00 D correction.

| Treatment Zone Diameter | Corneal Reshaping Tissue Displacement |
|---|---|
| 6.0 mm | 36 microns |
| 5.0 mm | 25 microns |
| 4.0 mm | 16 microns |
| 3.0 mm | 9 microns |

Based on the Munnerlyn formula it would appear that most of the optical changes in corneal reshaping can be attributed to changes in the epithelium. However, the possibility of long term changes in Bowman's layer and the stromal bed may also assist in achieving the desired optical result.

As mentioned above, previous orthokeratology technologies have used RGP contact lenses to achieve their corneal reshaping effects.

A currently favored theory as to how RGP orthokeratology works is that, for orthokeratology to correct myopia, a thin posterior tear layer is created when a lens with a central radius of curvature that is flatter (i.e. a greater radius of curvature) than that of the central cornea is placed on the eye. The resulting tear film creates a shear pressure beneath the lens that redistributes the corneal thickness from the center to the mid-periphery. This creates a positive "push" force on the center of the cornea by virtue of a thin (approximately 5 micron) tear layer across the central cornea. The steeper mid-peripheral curve of the lens creates a thick tear layer (approximately 550 microns) resulting in a negative "pull" pressure that contributes to the redistribution of the corneal thickness from the center to the mid-periphery. Together, these two forces create the desired topographical/optical changes seen in myopic orthokeratology. Within approximately 7 to 10 days of overnight lens wear, the procedure will have resulted in the required degree of central corneal flattening and mid-peripheral corneal steepening.

As is set out in more detail below, clinical tests on patients using everted soft contact lenses have found that an unexpectedly high level of optical correction can be achieved using soft lenses. As it would be particularly advantageous to provide the lens wear overnight, it is anticipated that soft lenses having an oxygen transmissibility of greater than about 87 barrers would be suitable for use with the invention (Holden B. A., Mertz G. W., *Critical oxygen levels to avoid corneal edema for daily and extended wear contact lenses*, INVEST OPHTHALMOL VIS SCI. 1984 25:1161-1167). Silicone hydrogel lenses designed in accordance with the teachings of this specification could be suitable for such treatment.

Whilst not wishing to be bound by theory, clinical results suggest that the present soft lens design does not primarily induce its orthokeratology effect by corneal tissue redistribution but instead by compression of the corneal tissue. It should be understood, however, that the present system and method may also include achieving desired effects through tissue redistribution, epithelial and corneal stromal cell generation and removal, cell migration or redirection, and changes in cell size, in addition to or instead of compression.

The concept of corneal reshaping with a soft contact lens first came to the notice of the inventors when a patient (L.E.) presented herself with symptoms of a slight decrease in visual acuity in both eyes. The patient had a one year history of successful 30-day continuous wear with the Focus Night and Day soft lens manufactured by CIBA Vision Corporation in Duluth, Ga. The patient had high refractive myopia and was, at that time, wearing the following soft contact lenses:

| Right Eye | |
|---|---|
| Base Curve: | 8.4 mm |
| Power: | −9.00 D |
| Diameter: | 13.8 mm |
| Right Eye | |
| Base Curve: | 8.4 mm |
| Power: | −9.00 D |
| Diameter: | 13.8 mm |

Unable to determine the nature of the patient's visual complaints, corneal topographical mapping of the patient's eyes was conducted with a Humphrey Atlas Topographer. The map clearly indicated that the topography (shape) of the patient's anterior cornea had been altered by the soft contact lenses. The topographical changes were most evident on the left eye which demonstrated a flattening over the central 3.0 mm of the cornea and mid-peripheral steepening.

It was then postulated that the patient may have inadvertently everted her soft contact lenses and had been wearing them everted for an unknown period of time. It was then agreed to perform a pilot study on the blind left eye of Patrick Caroline to determine if the wearing of an everted −9.00 diopter soft lens could indeed result in the topographical changes noted in the patient. A topographical map of Feb. 4, 2002 served as the baseline (FIG. 1).

On Wednesday, Feb. 12, 2003, Dr. Stacy Aboutalebi inserted an everted −9.00 diopter Focus Night and Day soft lens onto the left eye of Patrick Caroline. Mr. Caroline wore the lens from 10:00 AM until 5:45 PM. At that time a slit lamp examination was performed and the soft lens was noted to be centered on the eye and the cornea free of ocular pathology.

Figure 2:
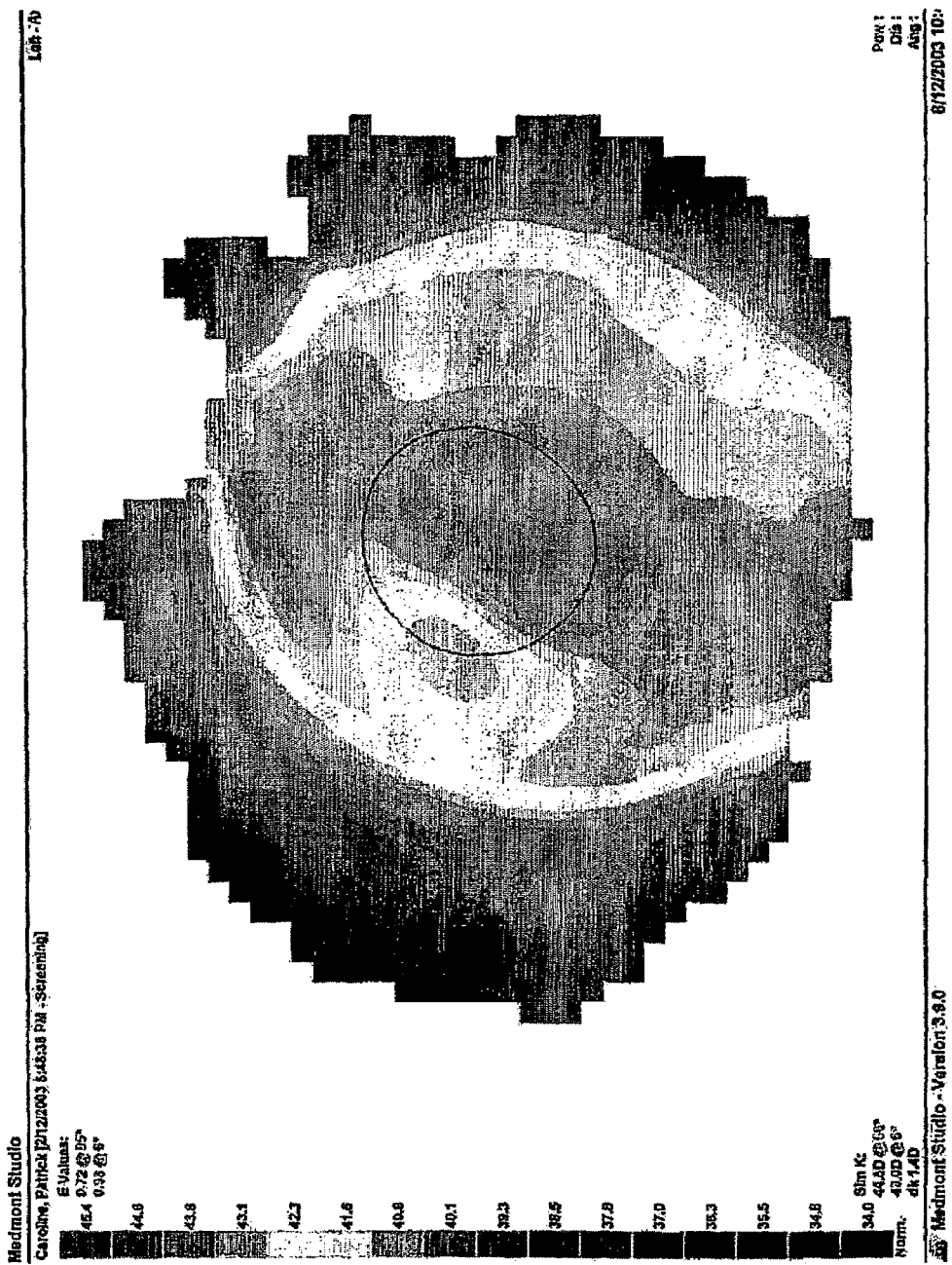

At 5:48 PM the soft lens was removed and corneal mapping performed with the Medmont Studio Corneal Topographer (FIG. 2). When the pre-fitting topography of the left eye was compared to that of the post-fitting topography, it was clear that significant corneal changes had resulted from the wearing of the everted soft contact lens.

Figure 3:
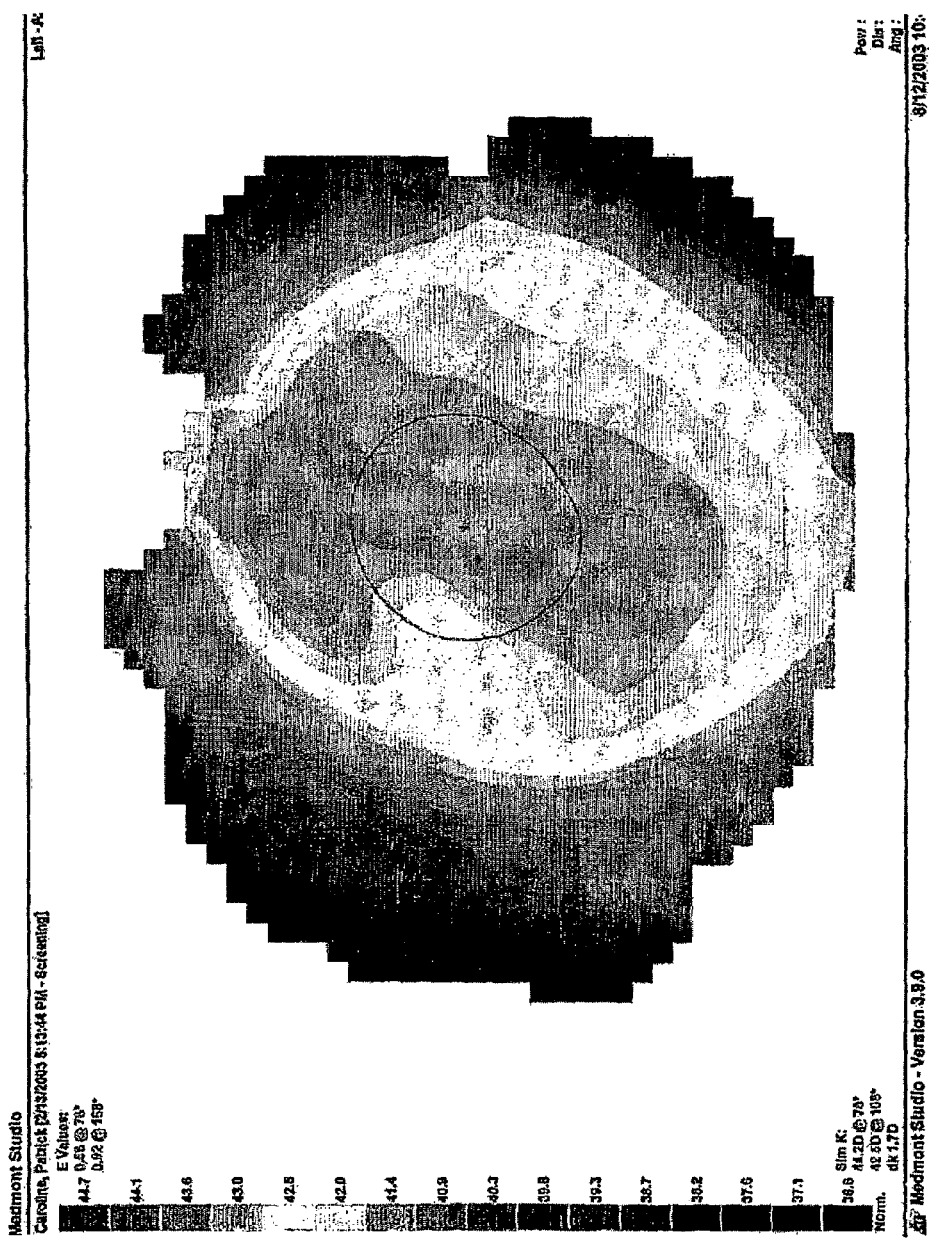

It was then decided that the soft lens should be reinserted and that Mr. Caroline should wear the lens overnight. He returned to Pacific University the next day Thursday, Feb. 13, 2003, wearing the soft lens. The lens was removed at 5:10 PM and corneal mapping performed (FIG. 3). Analysis of the map showed an increased amount of central corneal flattening.

Figure 4:
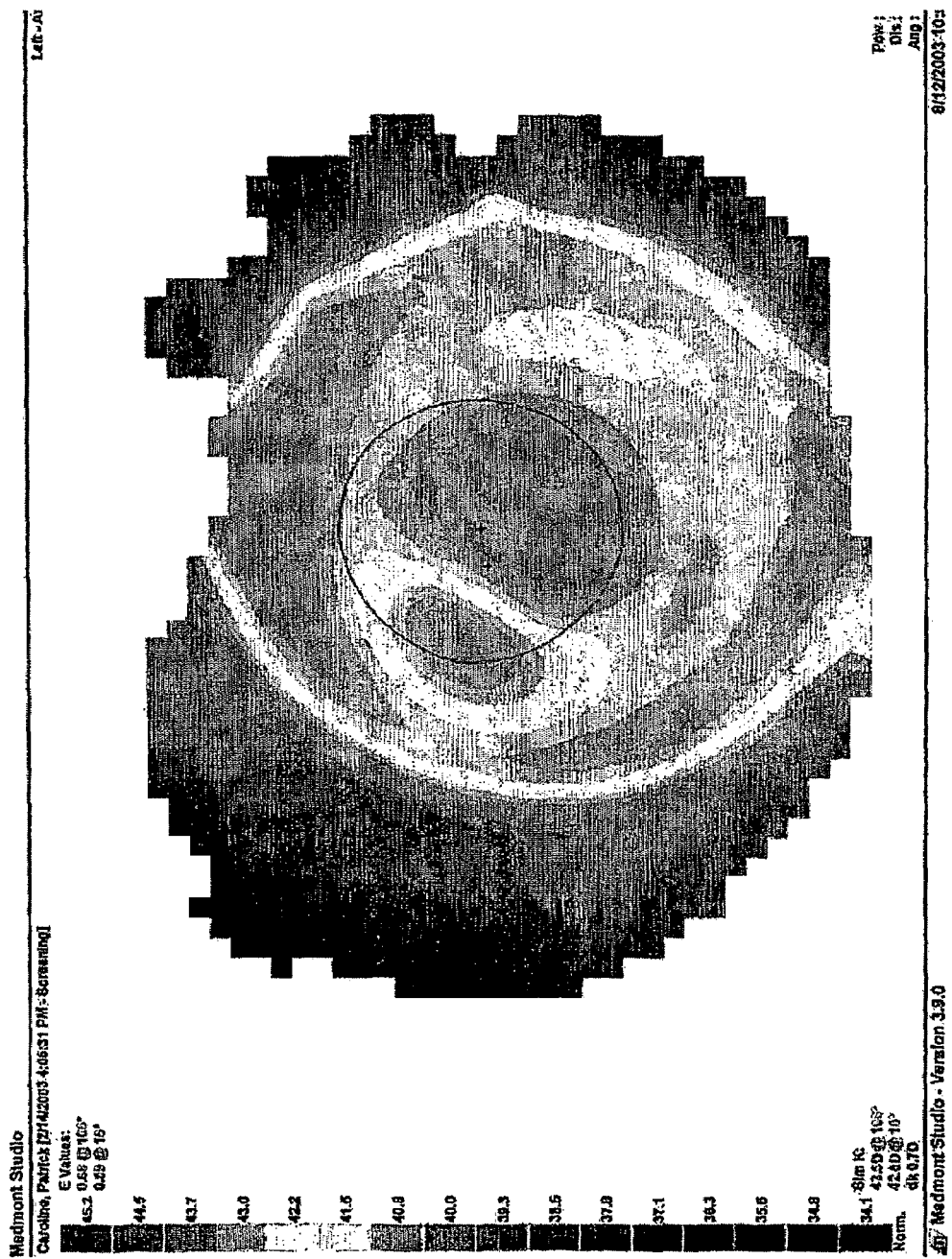

The following topographical maps show the progression of the corneal flattening over the next few days:

Friday, Feb. 14, 2003 (FIG. 4)

Figure 5:
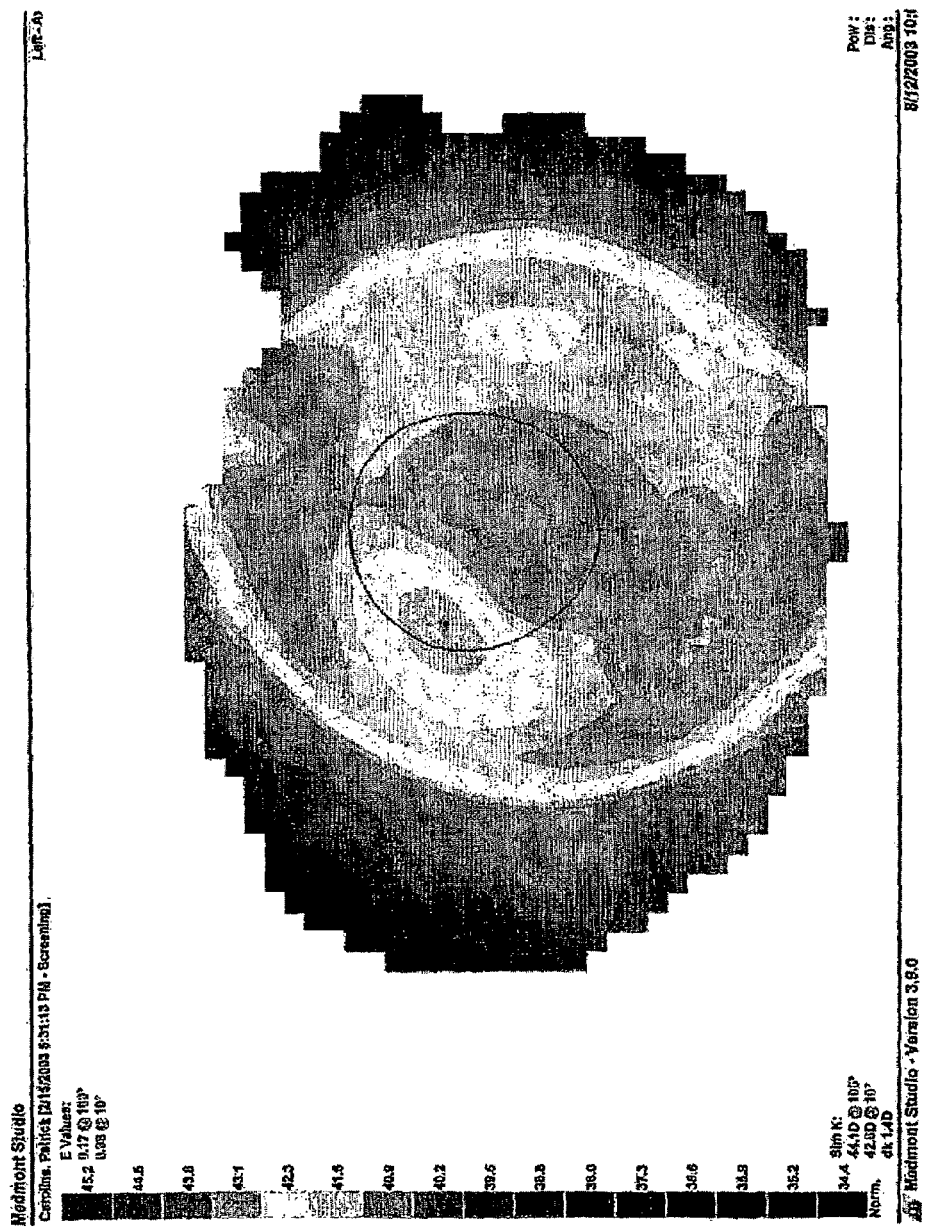

Saturday, Feb. 15, 2003 (FIG. 5)

From Feb. 15, 2003 to Mar. 1, 2003, a series of clinical trials were performed to validate the concept of soft contact lenses for orthokeratology. The results of these experiments further confirm the validity of the technique.

Figure 6:
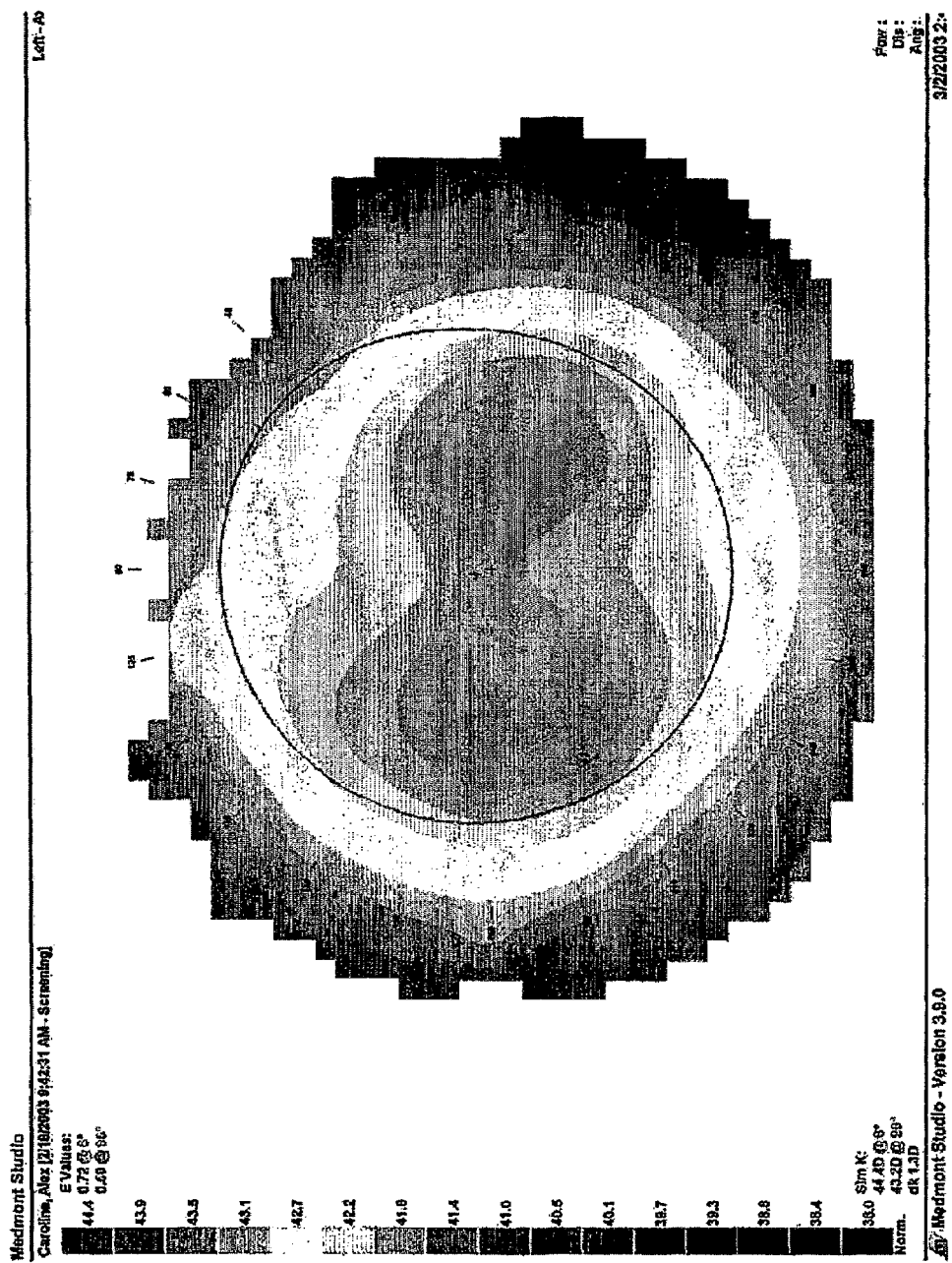

At 9:42 AM on Sunday Feb. 16, 2003, a baseline corneal topography measurement was taken on Alex Caroline's blind left eye (FIG. 6). At 9:50 AM an everted Ciba Focus Night and Day contact lens, with the following specifications, was inserted onto Alex's left eye:

| Base Curve: | 8.4 mm |
|---|---|
| Power: | −10.00 D |
| Diameter: | 13.8 mm |

Figure 7:
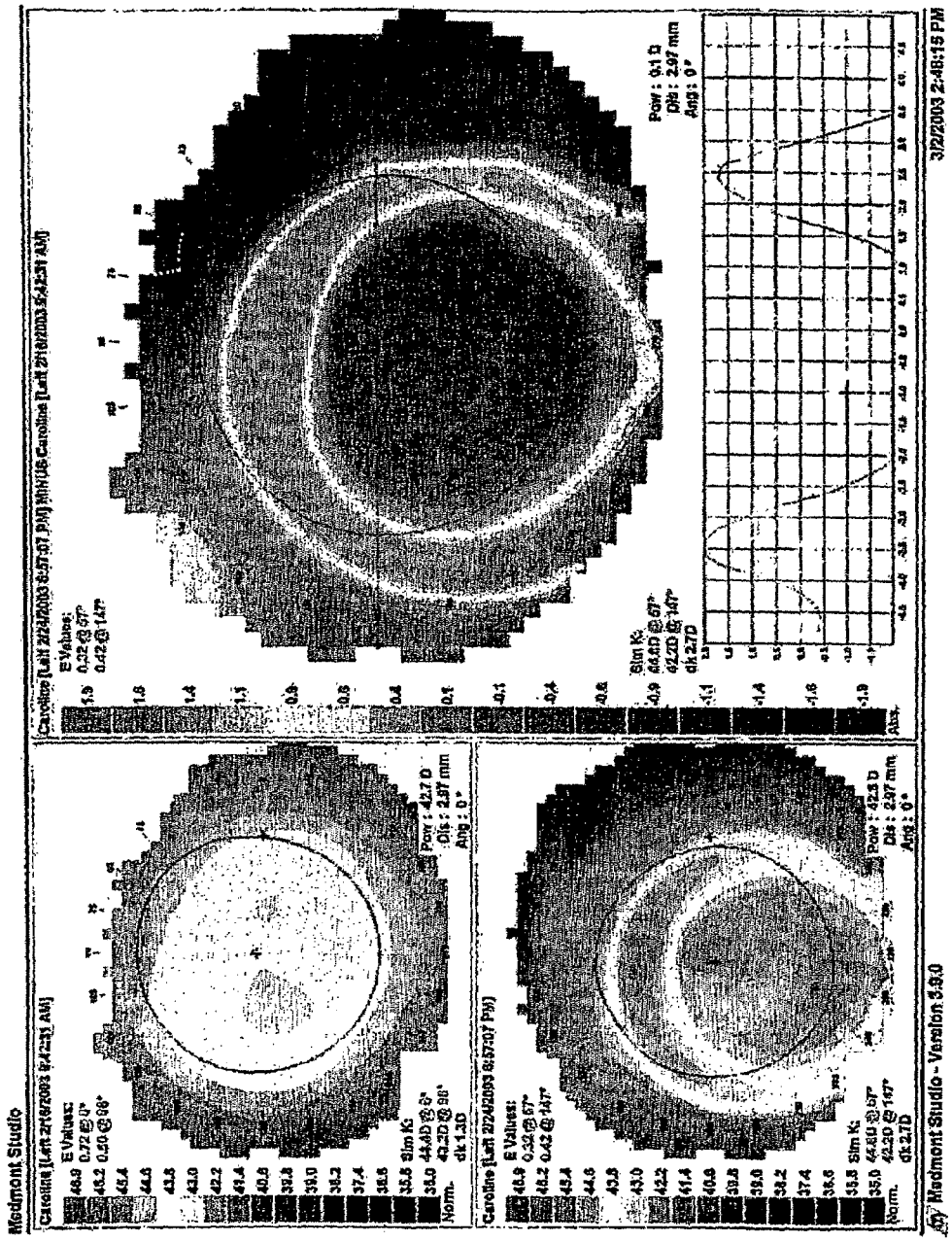
Figure 8:
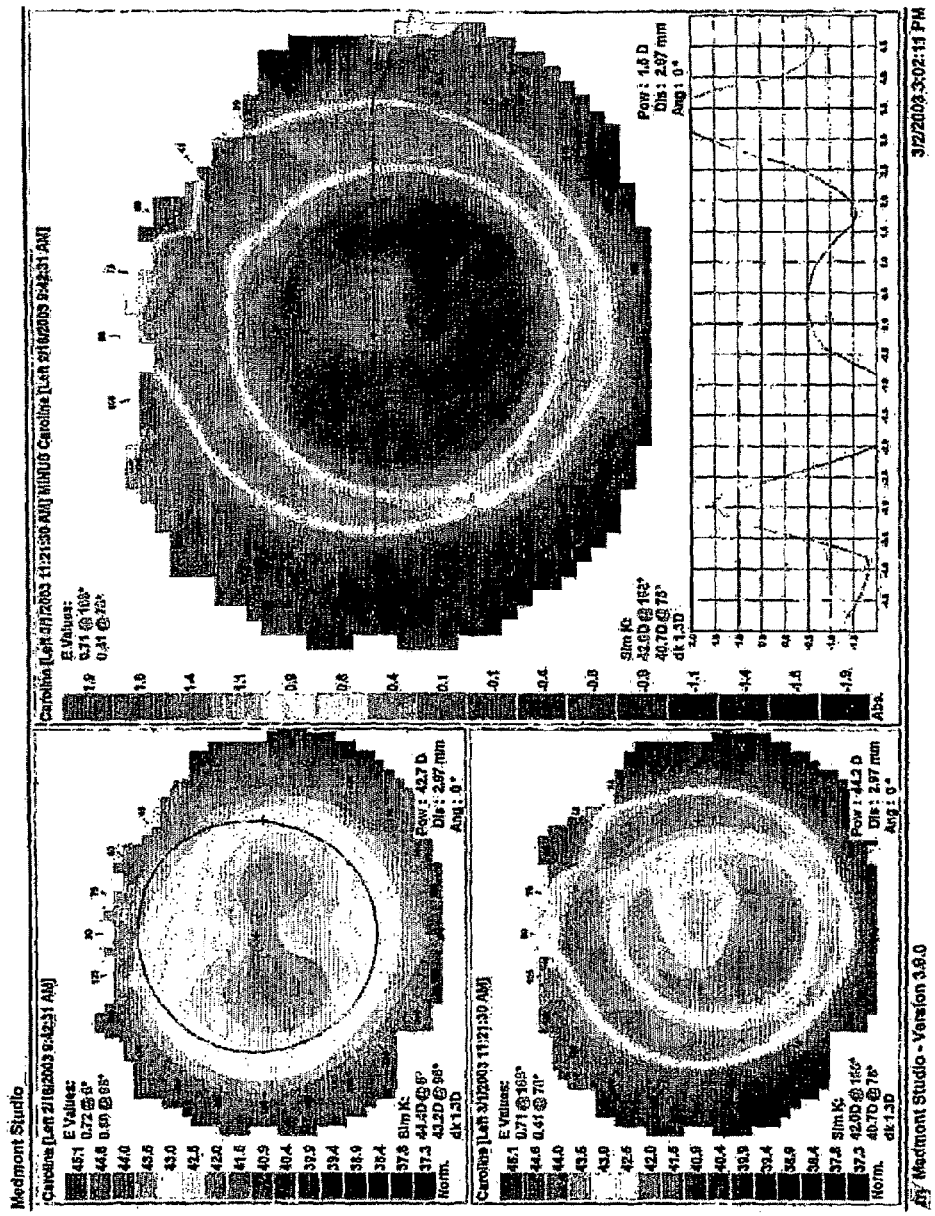

Alex wore the above everted contact lens continuously until Monday Feb. 24, 2003 at 6:56 PM. At that time the contact lens was removed and corneal topography was performed (FIG. 7). On Tuesday Feb. 25, 2003 the lens was again re-inserted, everted, onto Alex's left eye. On Mar. 1, 2003 at 11:20 AM, the contact lens was removed and corneal topography was performed (FIG. 8). The contact lens was again re-inserted, everted, onto Alex's left eye at 12:30 PM.

Figure 9:
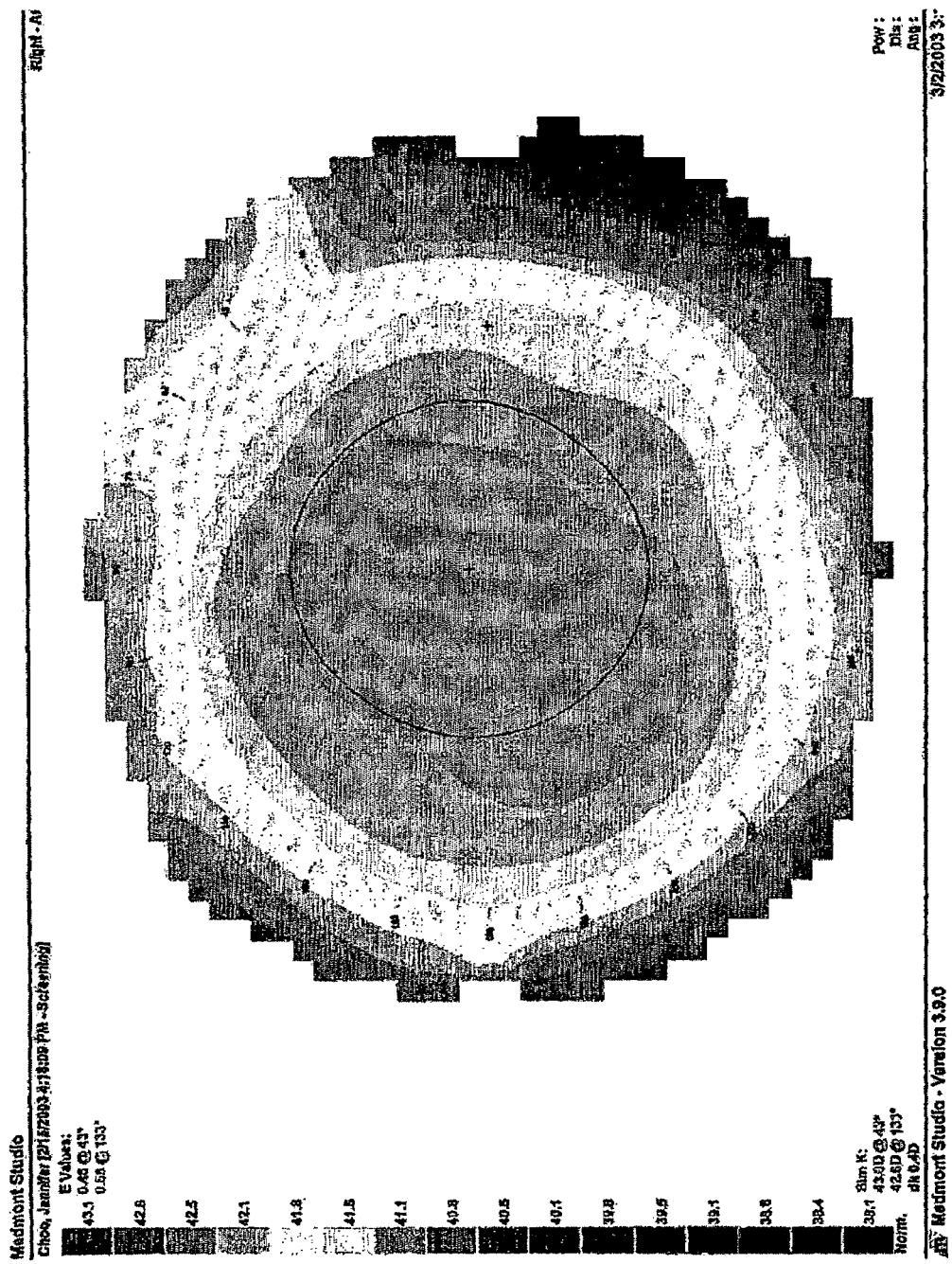
Figure 10:
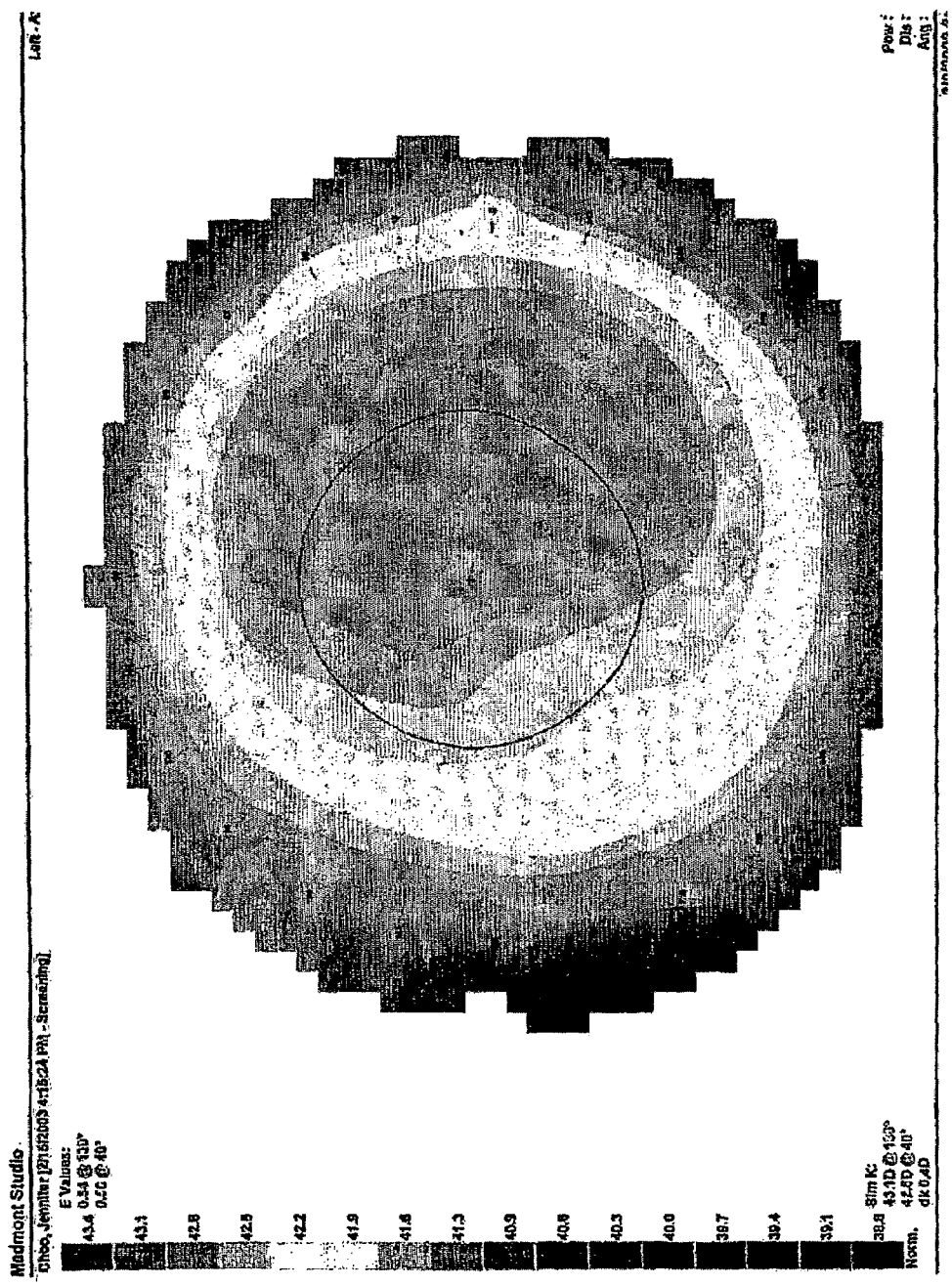

On Feb. 15, 2003 at 4:15 PM, baseline corneal topography was performed on Jennifer Choo (FIGS. 9 and 10). Jennifer's unaided acuities were 20/200 in each eye. Best corrected visual acuity was 20/20 in each eye with the following refraction:

OD: −4.00/−0.50×90

OD: −4.25/−0.25×90

At 5:00 PM Jennifer was fitted with the following everted contact lenses:

| Right Eye Purevision (Bausch and Lomb) | | Left Eye Focus Night & Day (Ciba) | |
|---|---|---|---|
| Base Curve: | 8.6 mm | Base Curve: | 8.6 mm |
| Power: | −4.50 D | Power: | −4.50 D |
| Diameter: | 13.8 mm | Diameter: | 13.8 mm |

Figure 11:
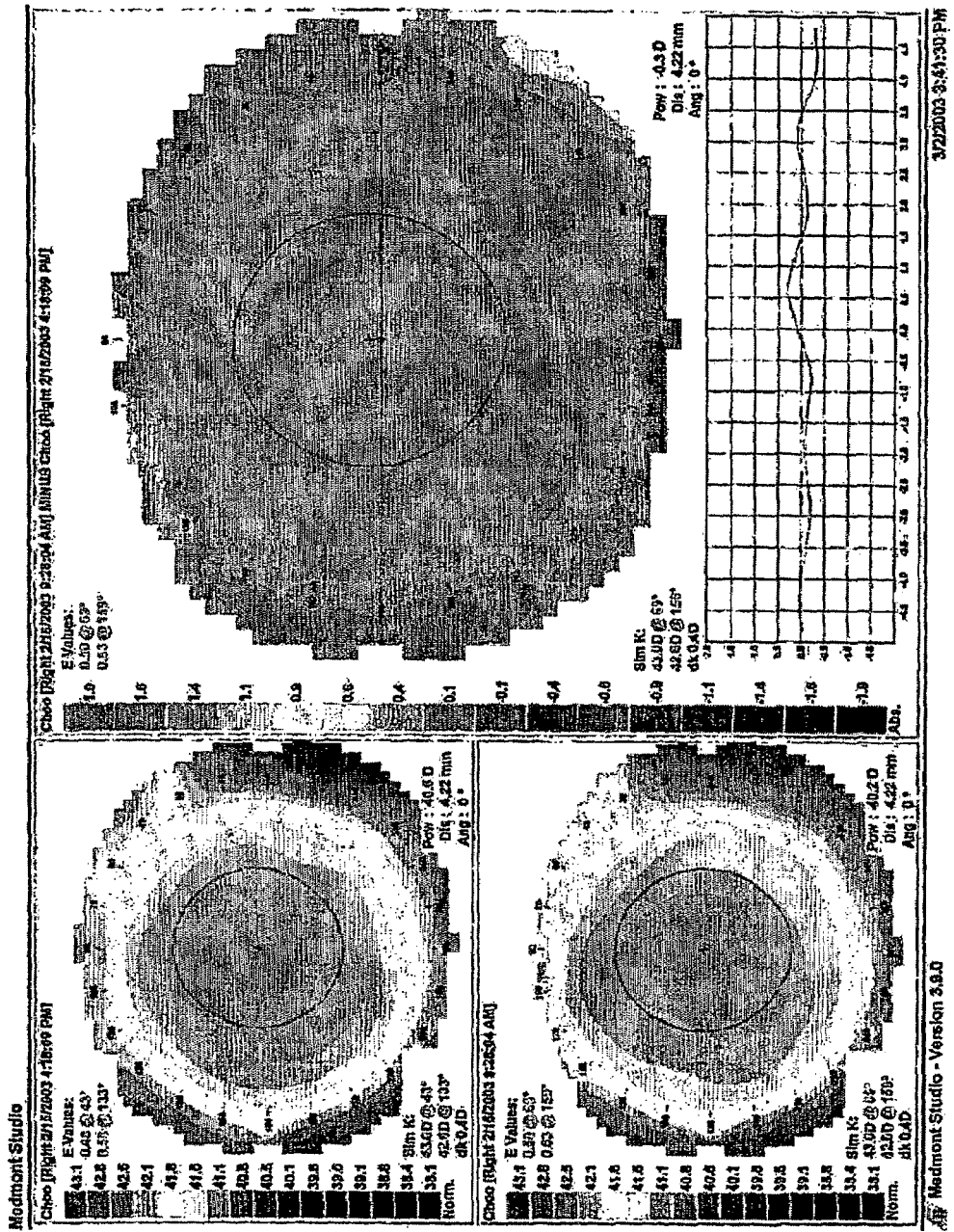
Figure 12:
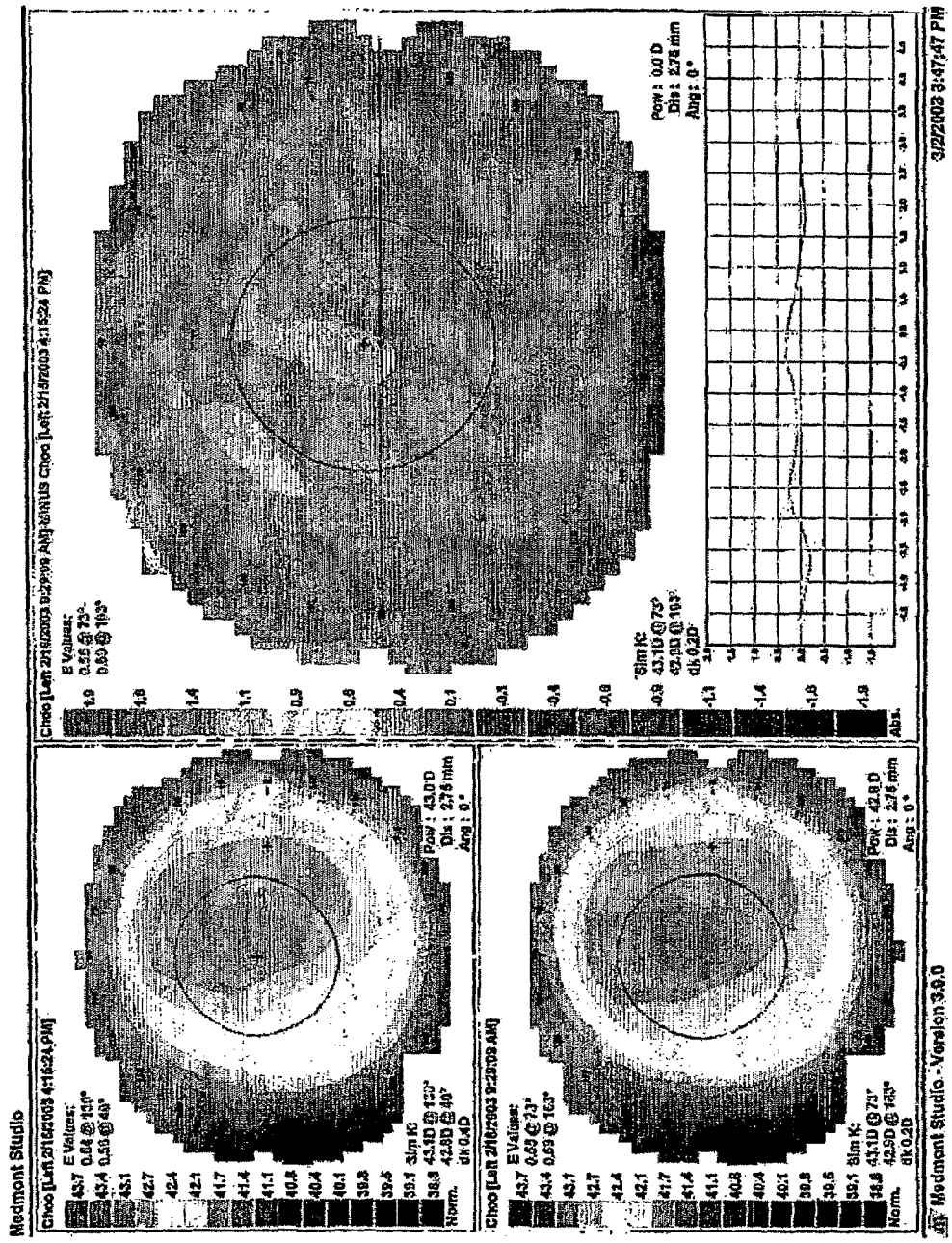

At 9:10 AM on Feb. 16, 2003 the contact lenses were removed and corneal topography was performed (FIGS. 11 and 12).

At 12:30 PM on Monday Feb. 17, 2003, Jennifer placed the following everted Focus Night and Day lenses on her eyes:

| Right Eye | | Left Eye | |
|---|---|---|---|
| Base Curve: | 8.6 mm | Base Curve: | 8.6 mm |
| Power: | −10.00 D | Power: | +6.00 D |
| Diameter: | 13.8 mm | Diameter: | 13.8 mm |

Figure 13:
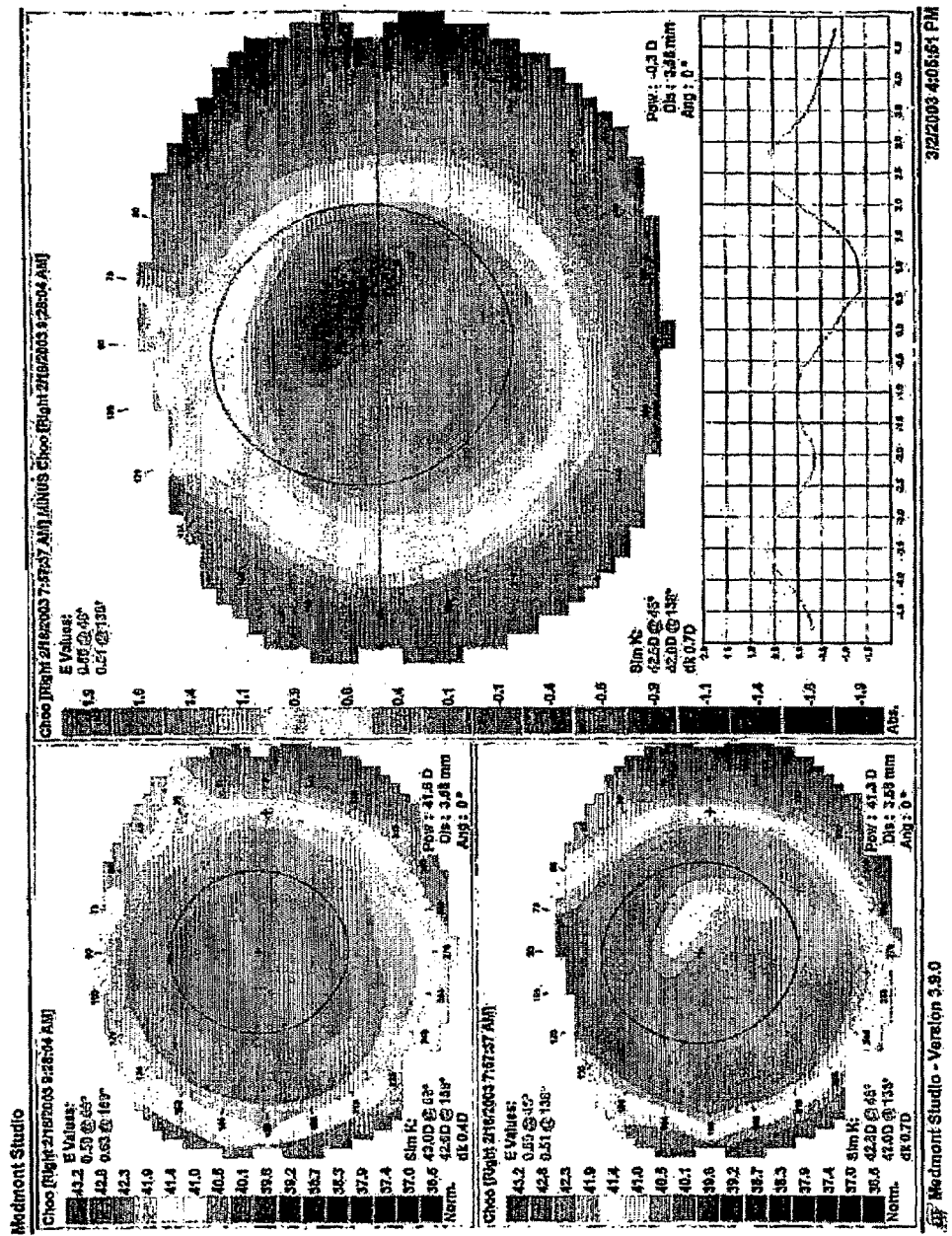
Figure 14:
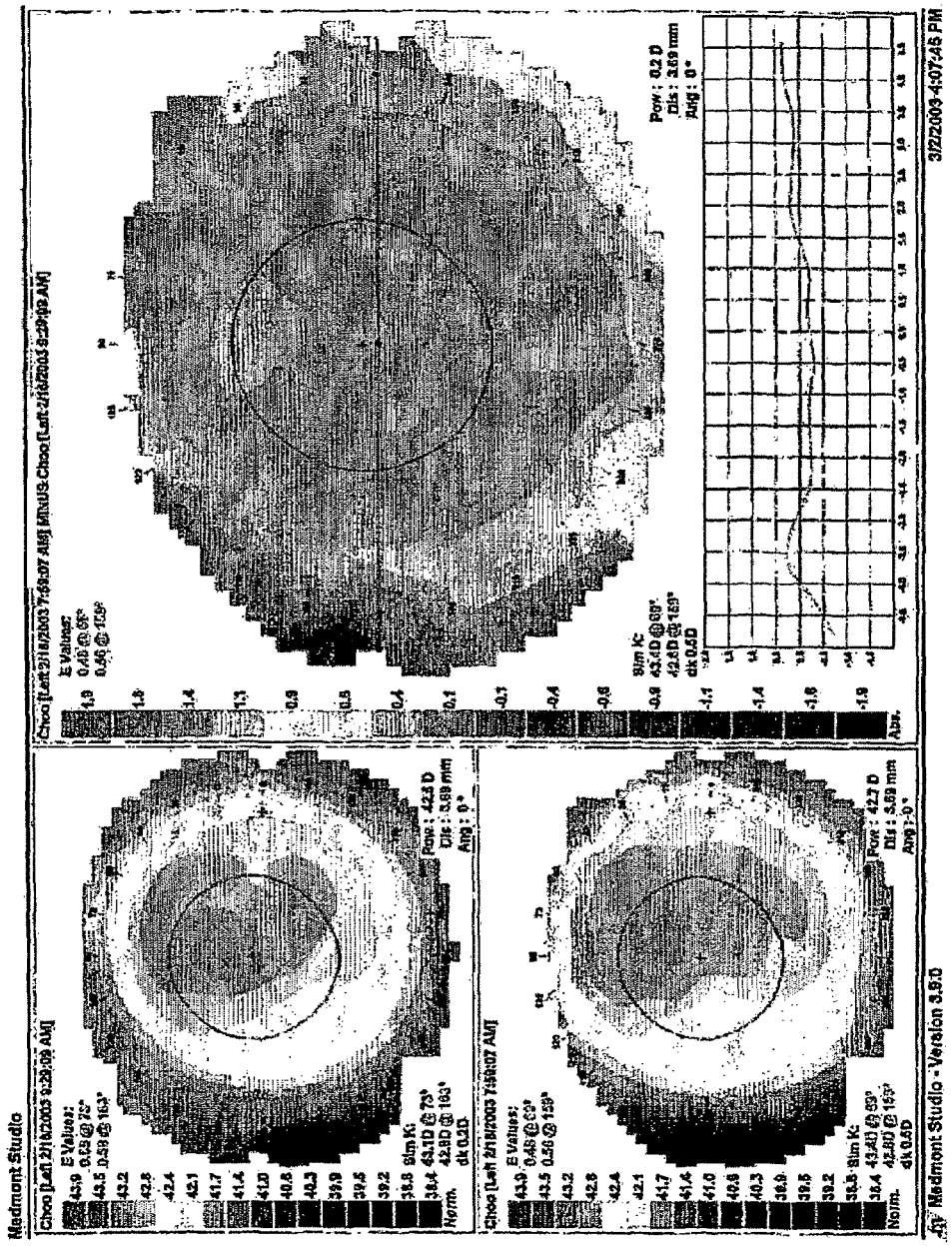

At 7:45 AM on Tuesday Feb. 18, 2003 the above contact lenses were removed and corneal topography was performed (FIGS. 13 and 14). Jennifer discontinued all contact lens wear until Thursday Feb. 27, 2003.

Figure 15:
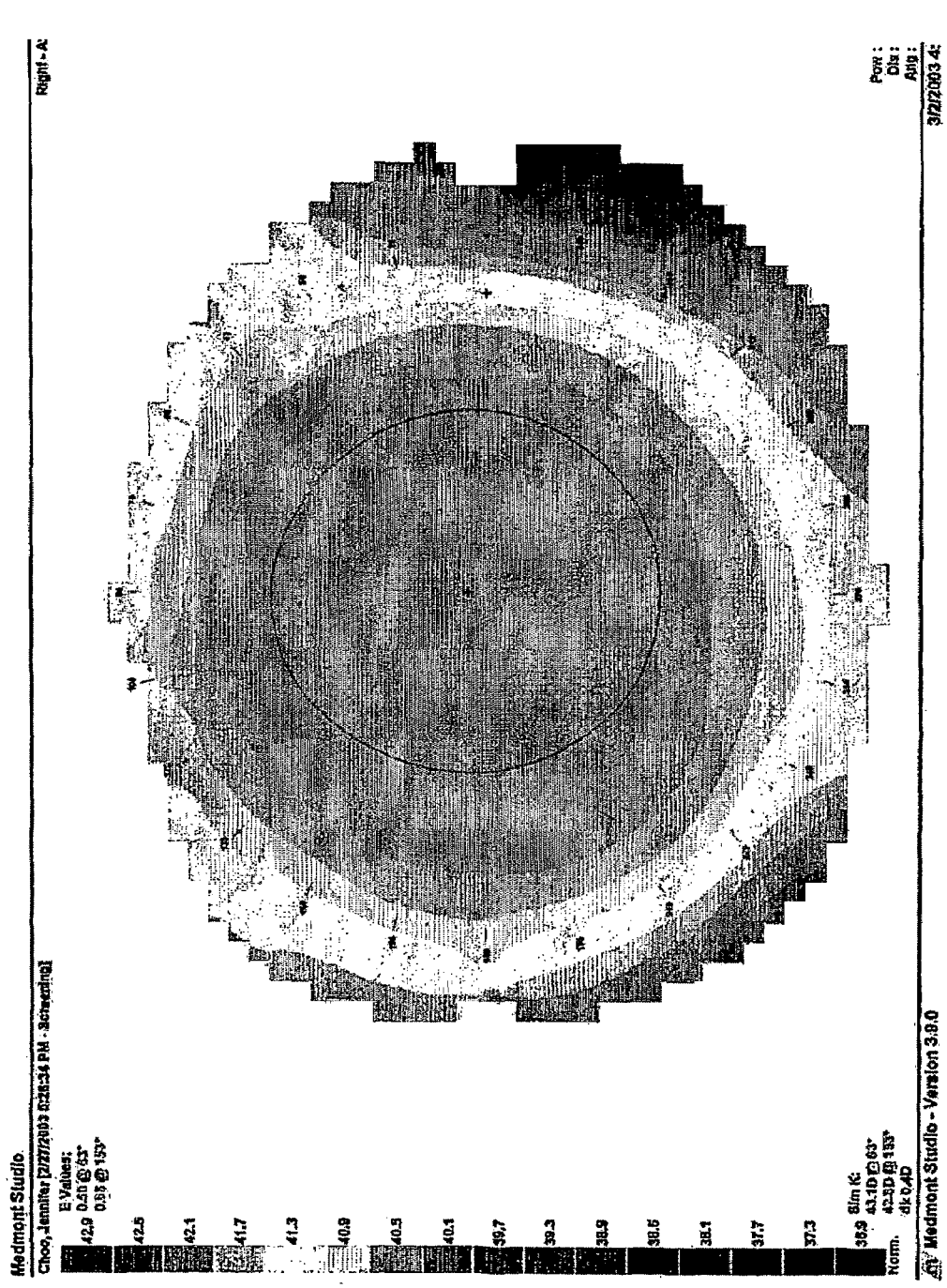
Figure 16:
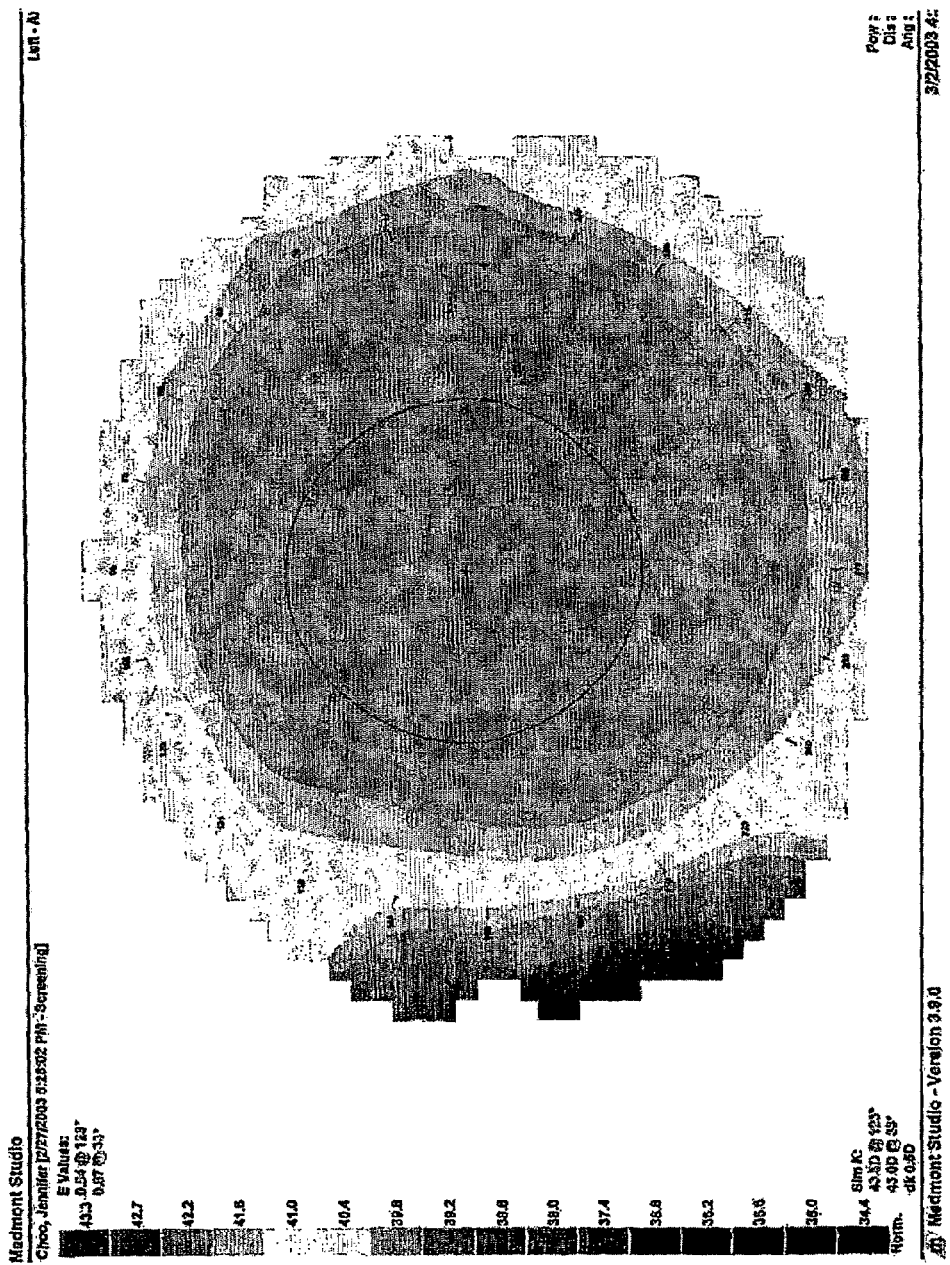

On Thursday Feb. 27, 2003 at 5:28 PM another baseline corneal topography was performed on Jennifer Choo (FIGS. 15 and 16). Focus Night and Day contact lenses with the following specifications were placed everted on Jennifer Choo's right and left eyes at 11:45 PM:

| Base Curve: | 8.6 mm |
|---|---|
| Power: | −10.00 DS |
| Diameter: | 13.8 mm |

Figure 17:
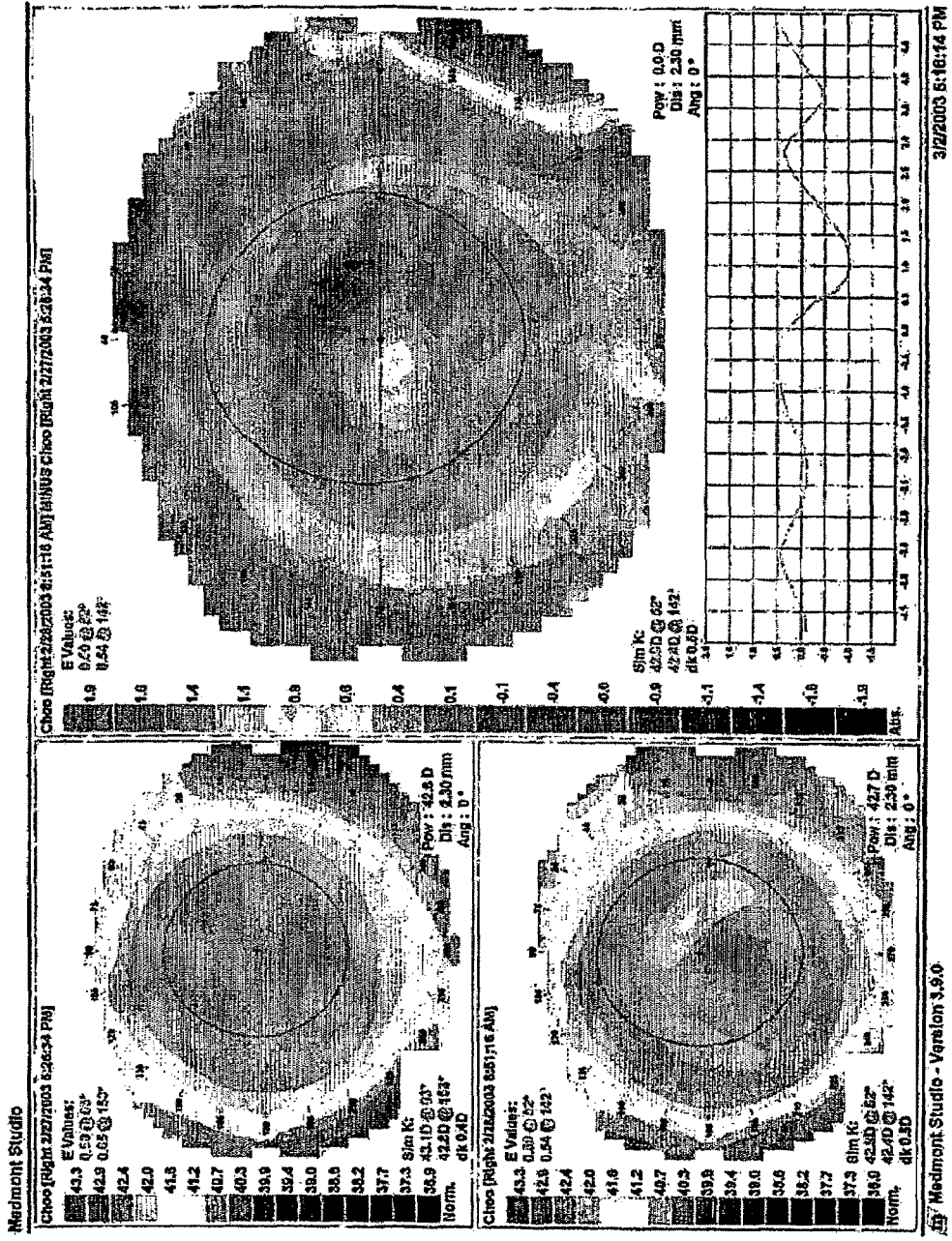
Figure 18:
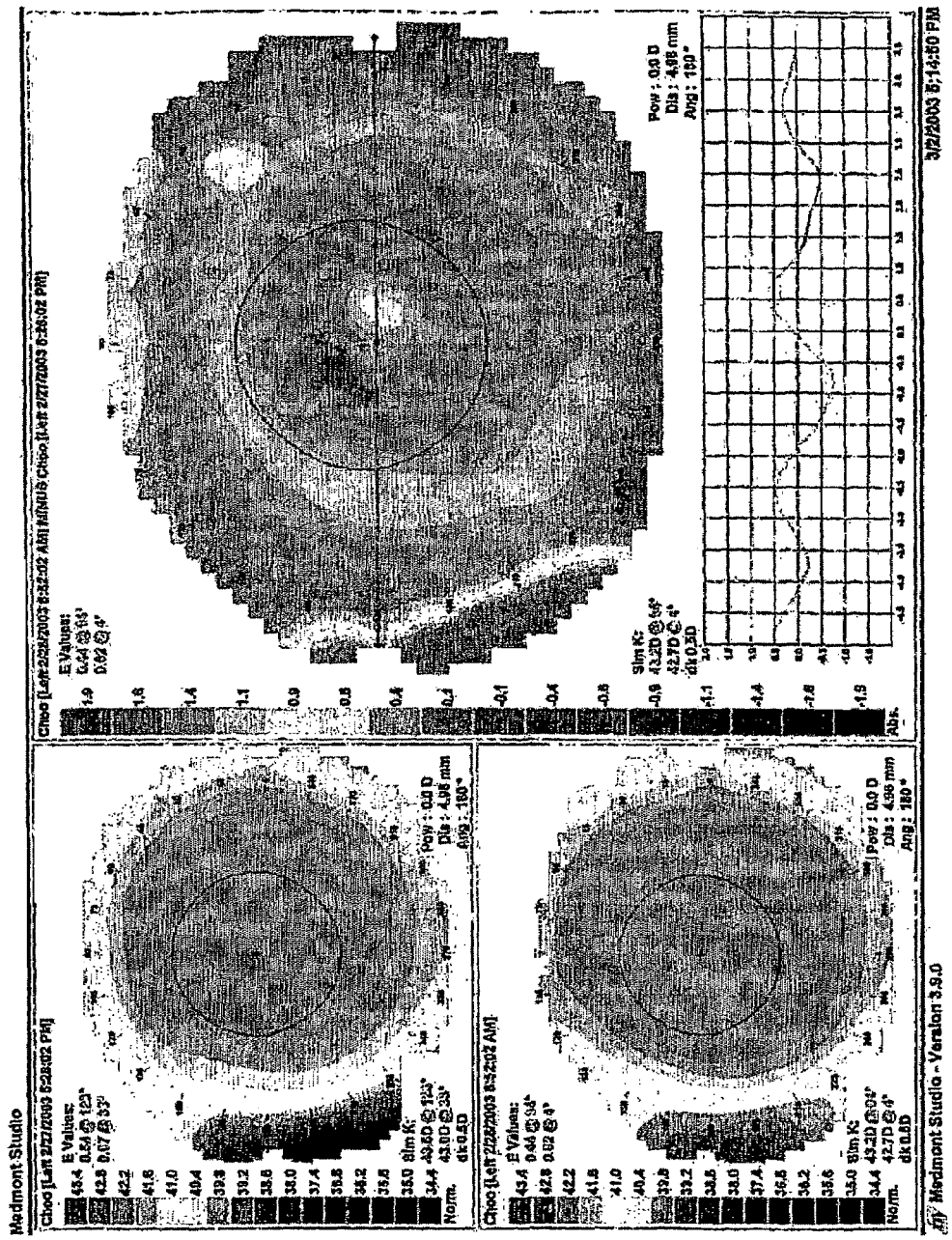

The contact lenses were removed at 7:30 AM on Friday Feb. 28, 2003. Corneal topography was performed on that same day at 8:30 AM (FIGS. 17 and 18). Jennifer's unaided acuities were 20/200 in each eye. Best corrected visual acuity was 20/20 in each eye with the following balanced refraction:

OD: −3.00/−0.50×90

OS: −3.25/−0.50×92

The same contact lenses were re-inserted everted onto Jennifer's eyes at 11:30 PM.

Figure 19:
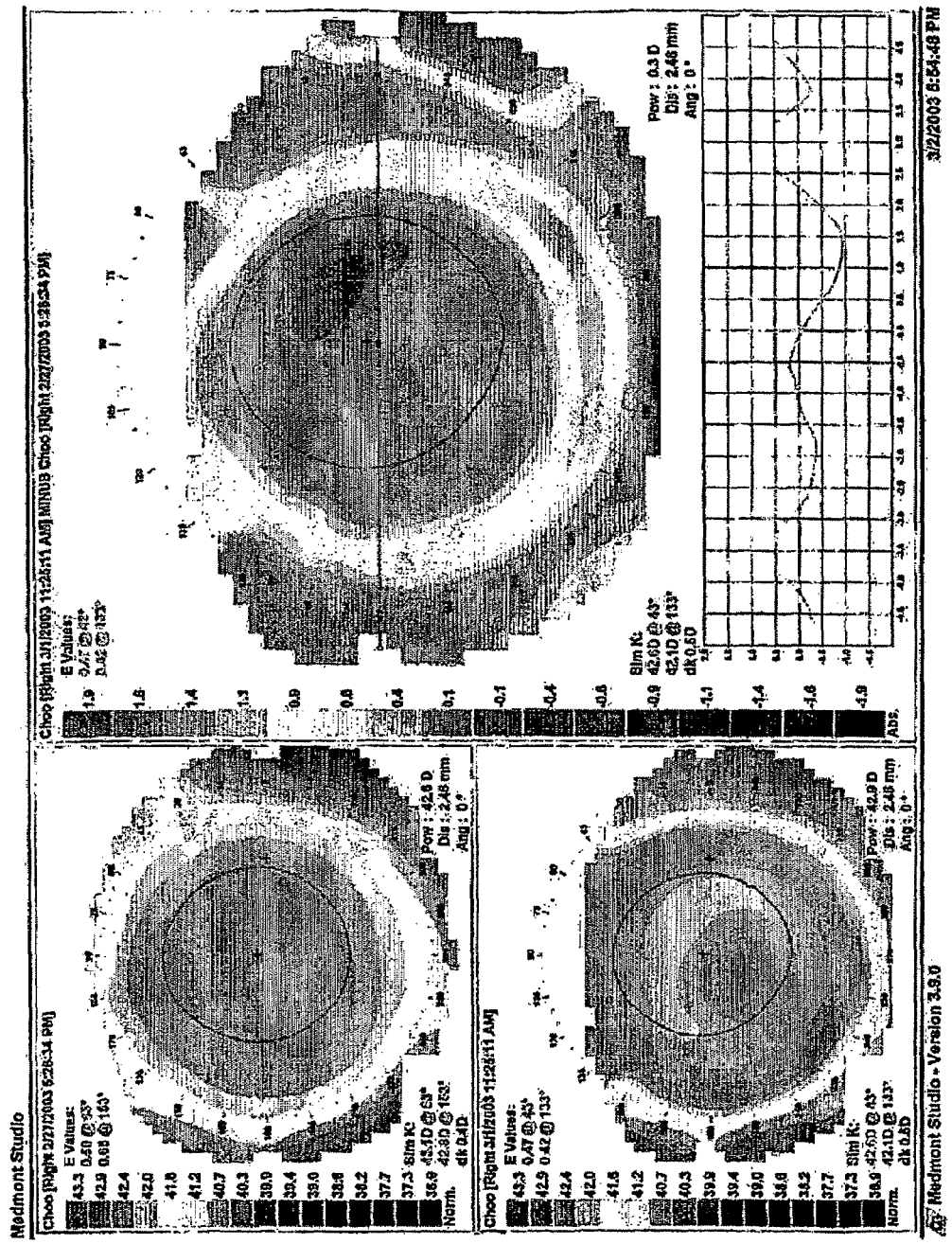
Figure 20:
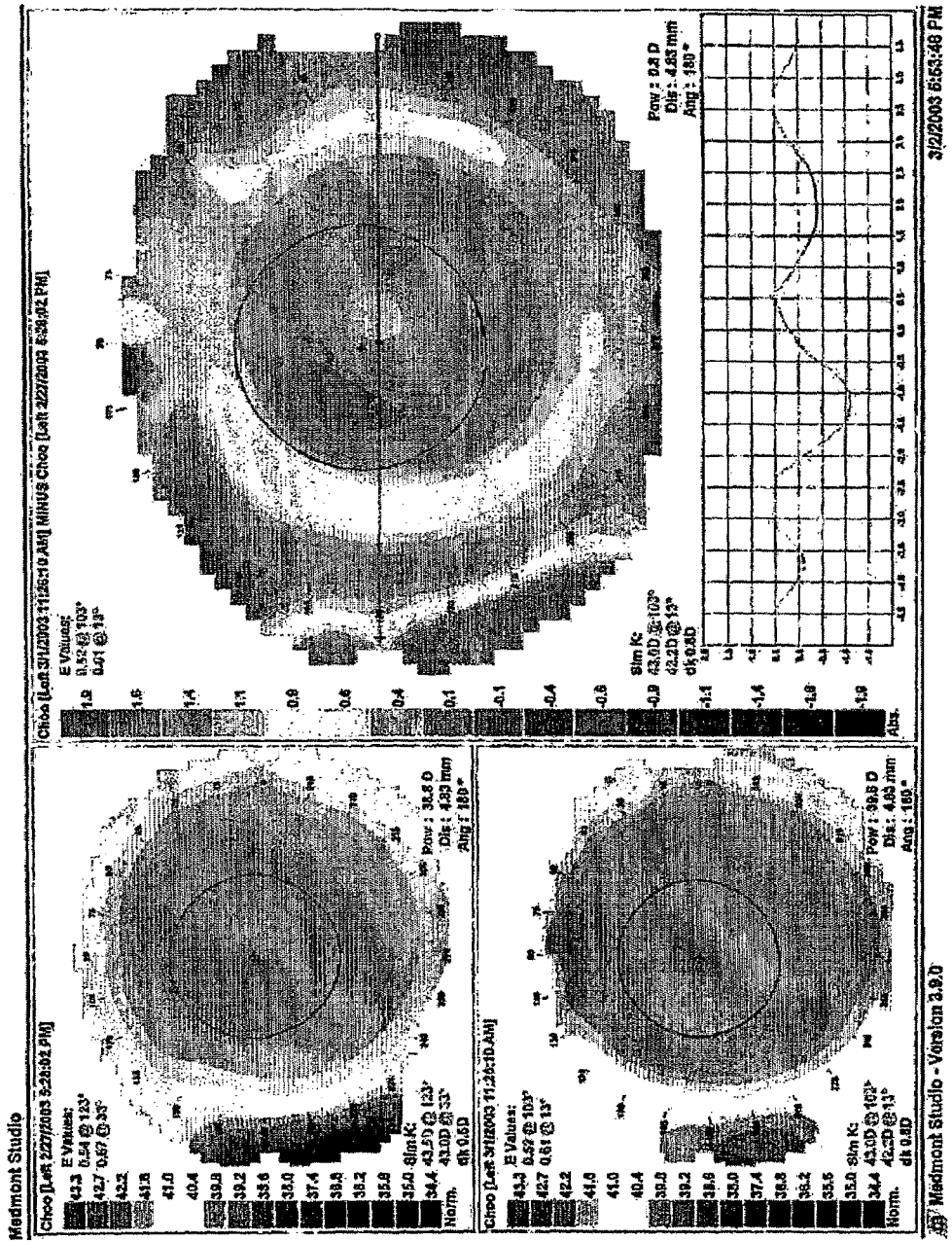

At 10:00 AM on Saturday Mar. 1, 2003, the contact lenses were removed. Corneal topography was performed at 11:21 AM (FIGS. 19 and 20). Jennifer's unaided visual acuity was 20/200 in each eye. She was best corrected to 20/20 in each eye with the following balanced refraction:

OD: −3.00 DS

OS: −3.25 DS

At 12:00 PM on Saturday Mar. 1, 2003, Jennifer wore the following everted Focus Night and Day contact lenses:

| Right Eye | | Left Eye | |
|---|---|---|---|
| Base Curve: | 8.6 mm | Base Curve: | 8.6 mm |
| Power: | −9.50 D | Power: | −9.50 D |
| Diameter: | 13.8 mm | Diameter: | 13.8 mm |

On top of the above contact lenses, Jennifer also wore the following non-everted Focus Night and Day contact lenses:

| Base Curve: | 8.6 mm | Base Curve: | 8.6 mm |
|---|---|---|---|
| Power: | +6.00 D | Power: | +5.75 D |
| Diameter: | 13.8 mm | Diameter: | 13.8 mm |

Figure 21:
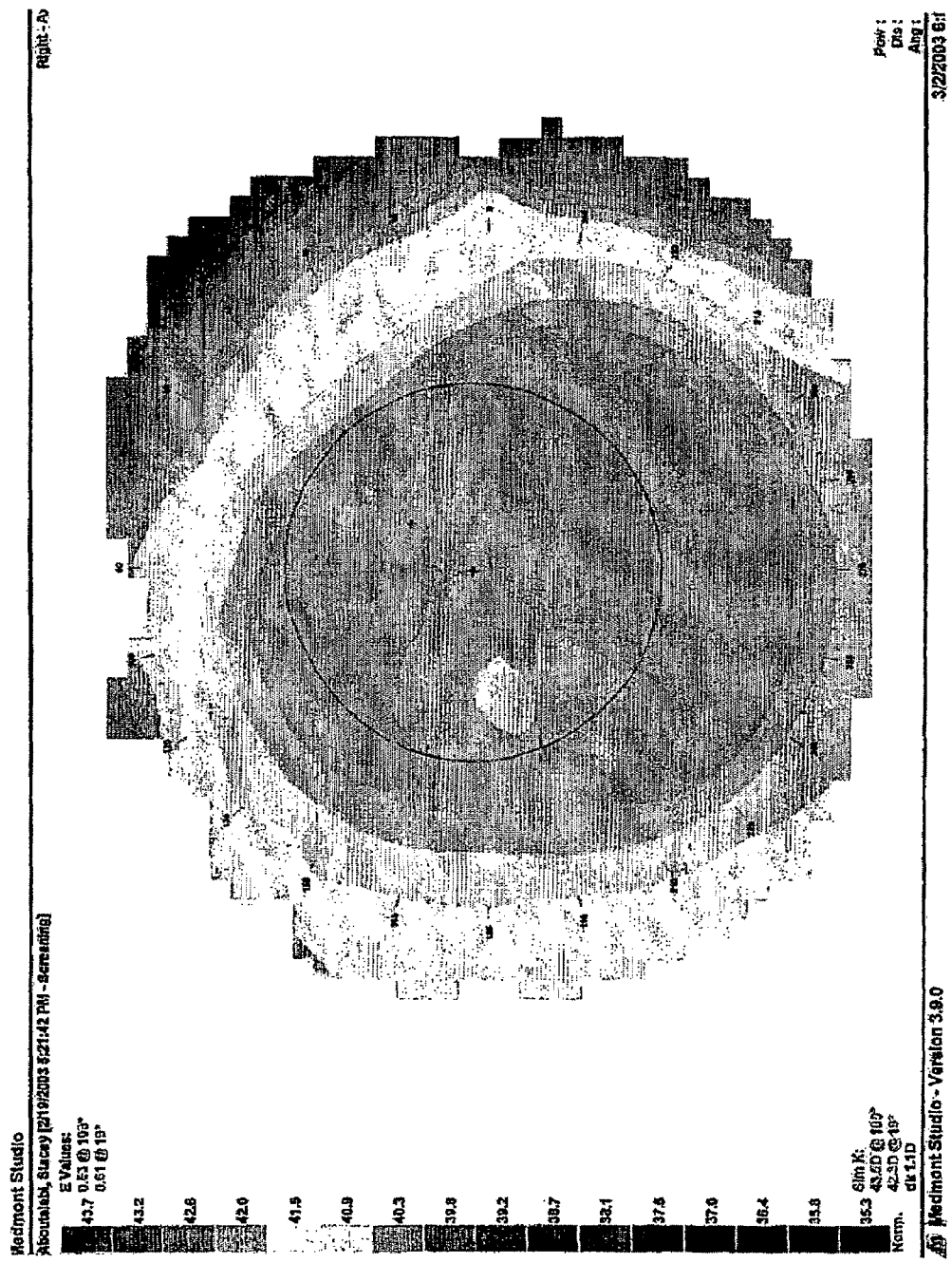
Figure 22:
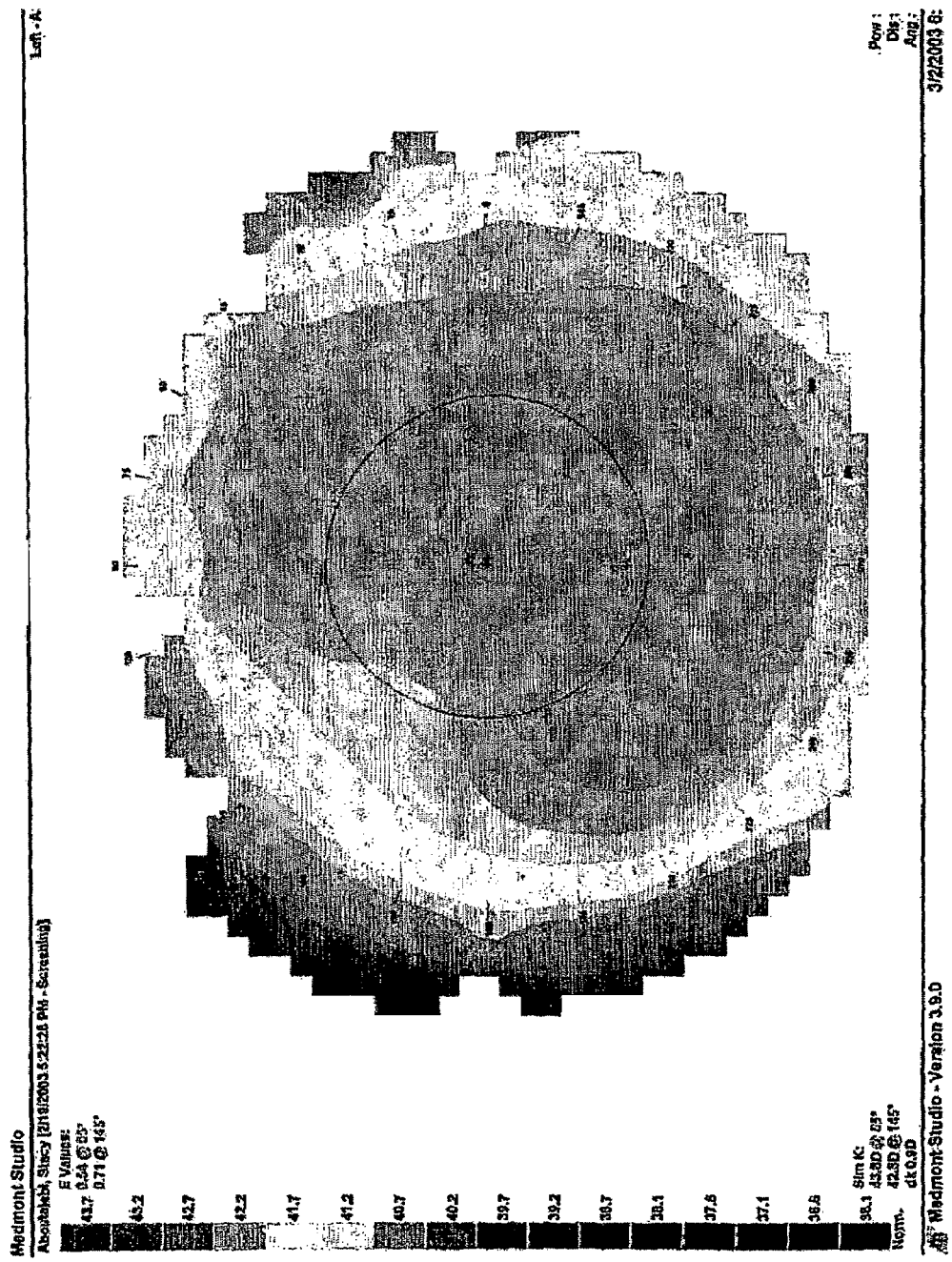

At 5:20 PM on Wednesday, Feb. 19, 2003, baseline corneal topography measurements were performed on Dr. Stacy Aboutalebi (FIGS. 21 and 22). Dr. Aboutalebi's unaided acuities were 20/100 in each eye. Best corrected visual acuity was 20/20 in each eye with the following balanced refraction:

OD: −1.25/−0.75×60

OS: −1.50/−1.00×115

At 10:30 PM on Thursday Feb. 27, 2003, Dr. Aboutalebi wore the following everted Focus Night and Day contact lenses on each eye:

| Base Curve: | 8.6 mm |
|---|---|
| Power: | −10.00 D |
| Diameter: | 13.8 mm |

Figure 23:
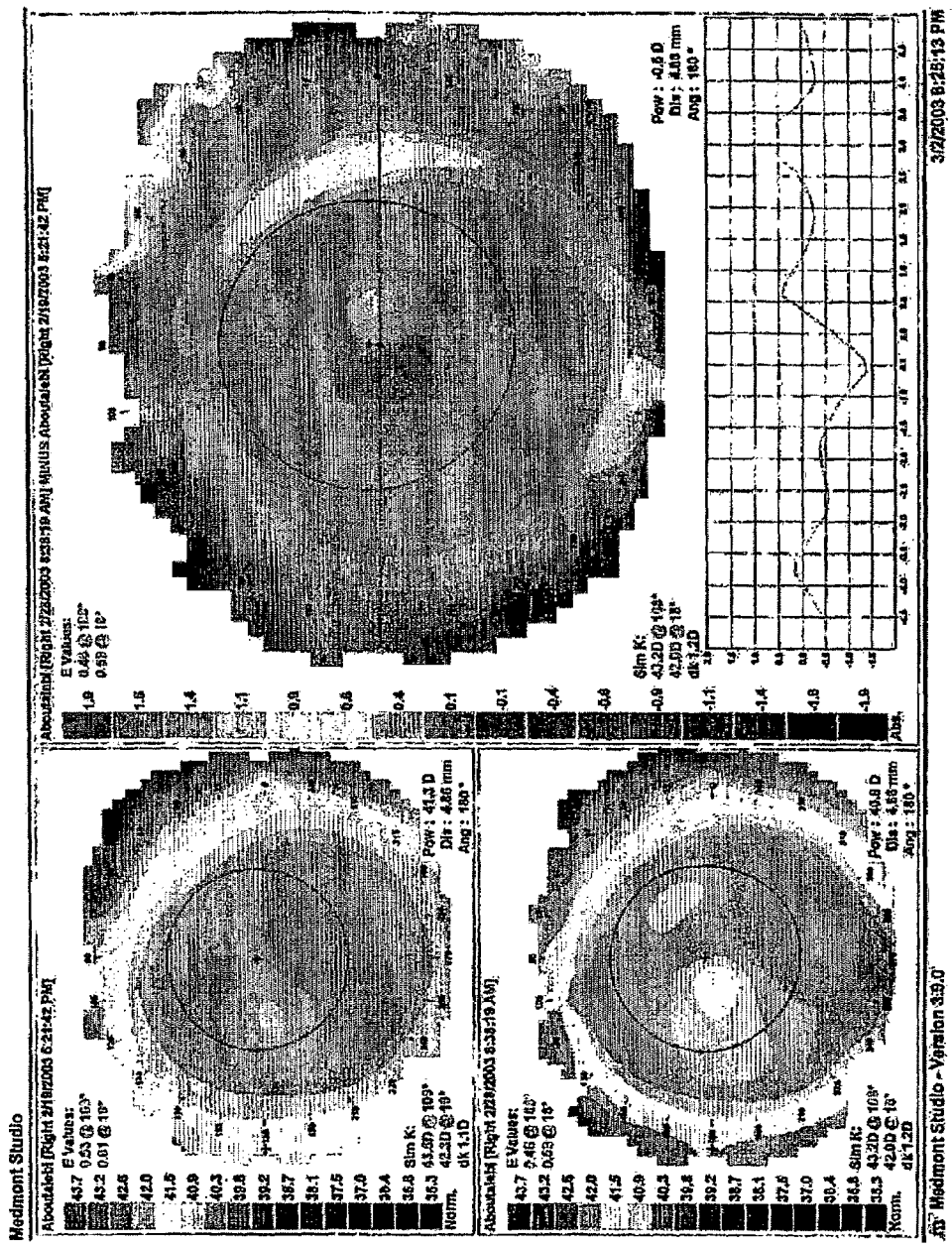
Figure 24:
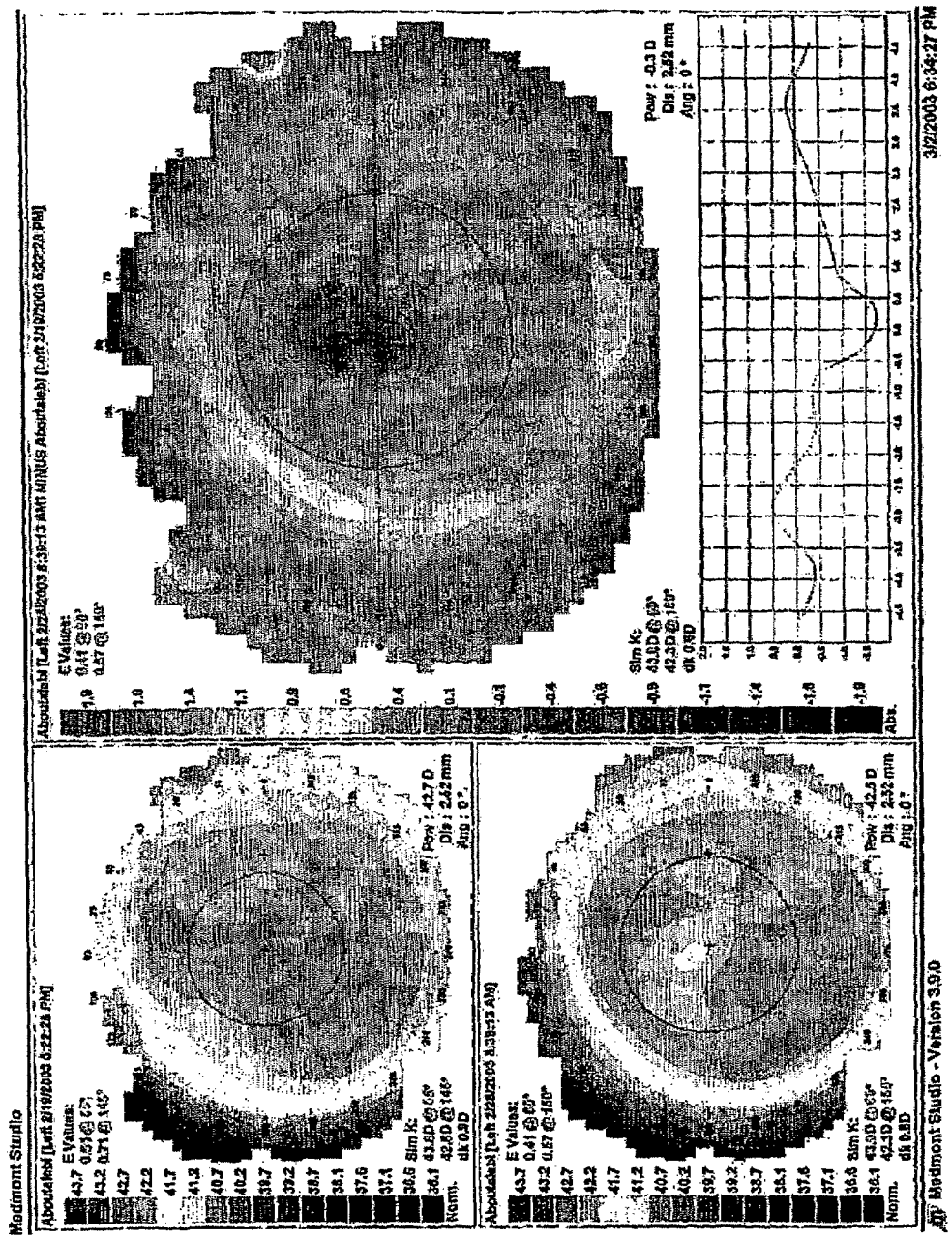

The above contact lenses were removed at 6:30 AM on Friday Feb. 28, 2003. Corneal topography was performed at 8:39 AM (FIGS. 23 and 24). Dr. Aboutalebi's unaided visual acuity was 20/25−1 in the right and 20/30 in the left eye using a Snellen Visual Acuity Chart. She was best corrected to 20/20 in each eye with the following refraction:

OD: −0.25/−0.75×58

OS: −0.25/−1.00×115

Figure 25:
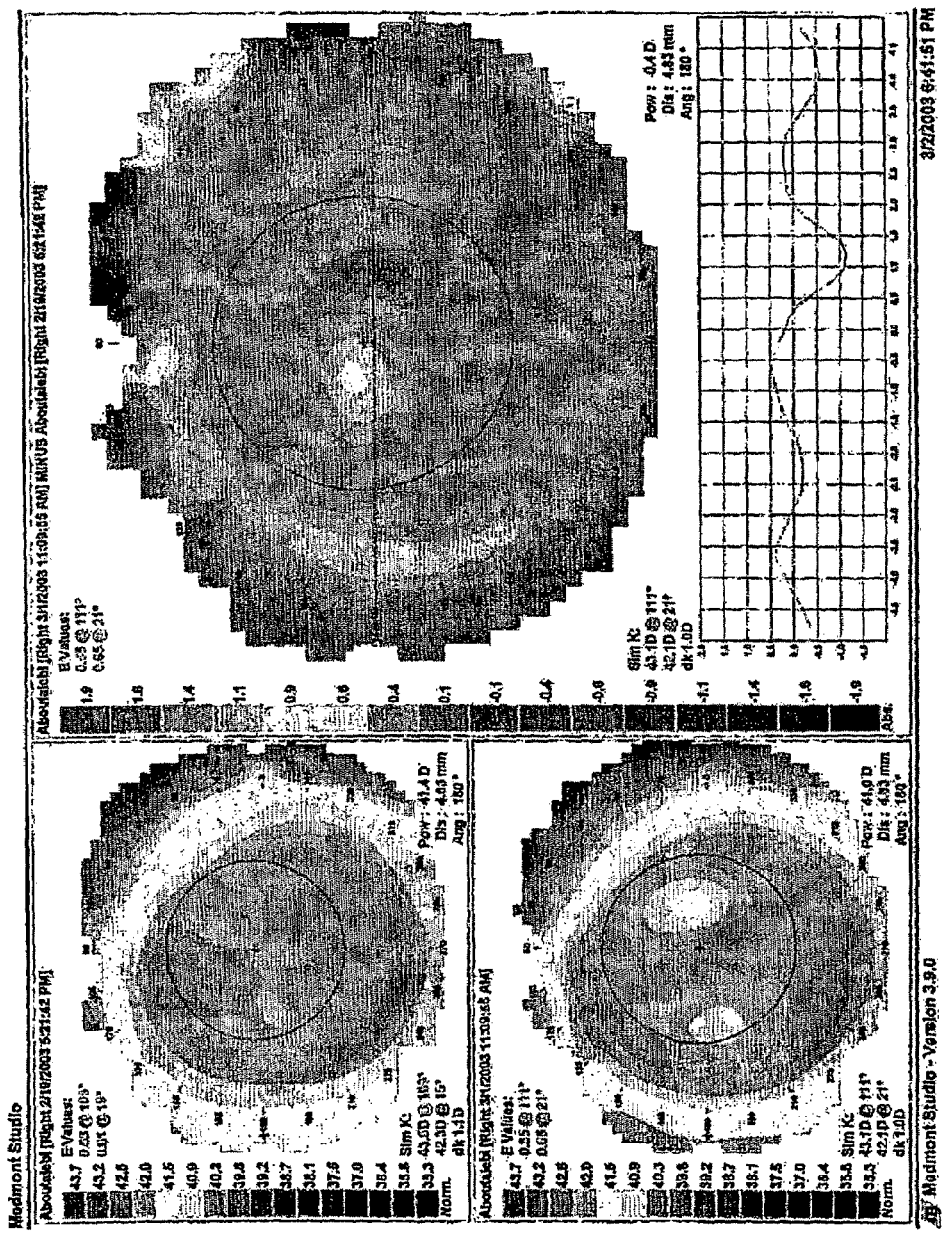
Figure 26:
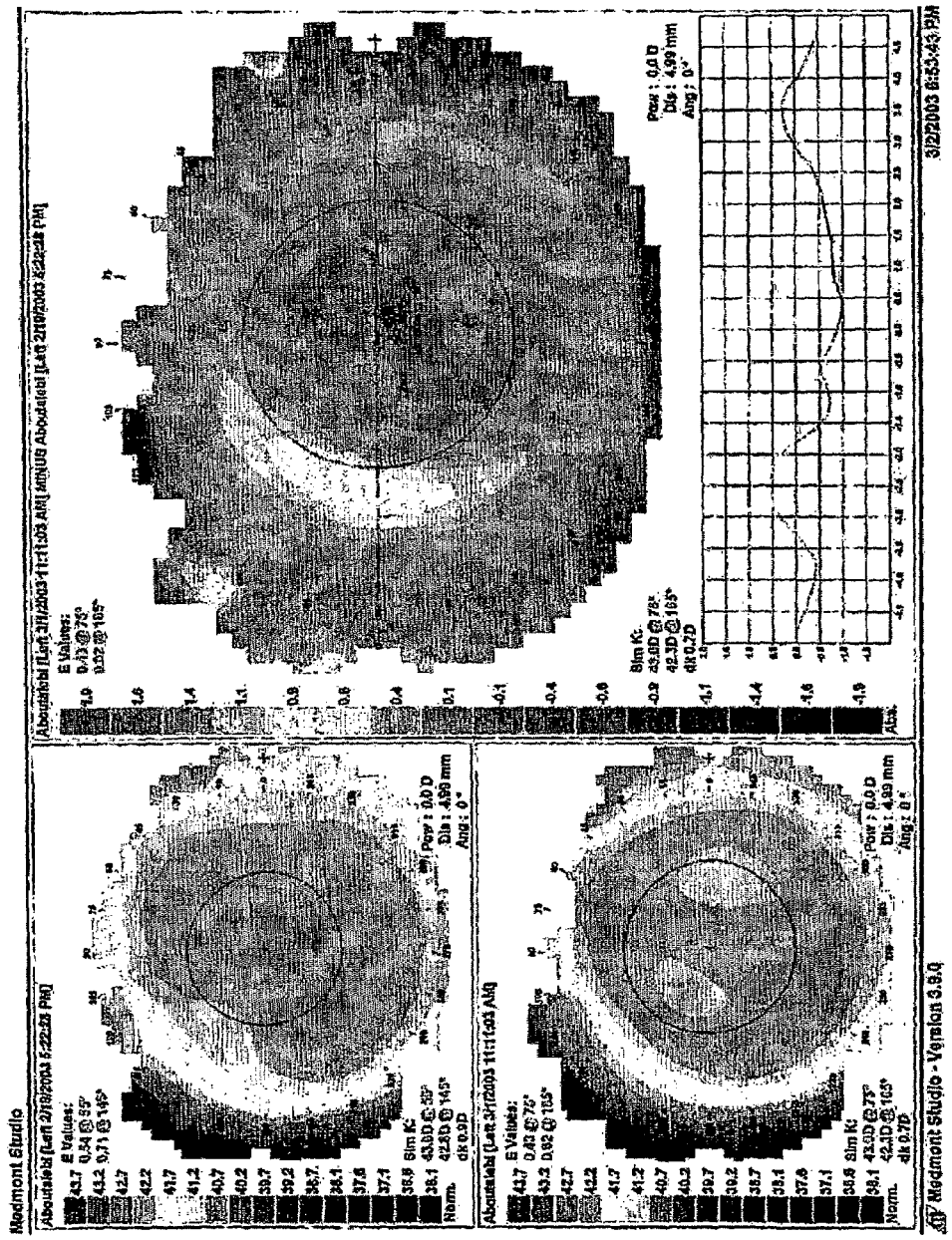

The contact lenses were re-inserted everted on Friday Feb. 28, 2003 at 10:40 PM and removed on Saturday Mar. 1, 2003 at 9:30 AM. Corneal mapping was performed at 11:09 AM (FIGS. 25 and 26).

It would be clear from the foregoing experimental results that reshaping of the surface layer of the cornea is possible using soft contact lenses. It is believed that the pressure applied to the eye surface by or via the lens, and the pressure gradients between zones of high pressure and zones of low pressure determines the nature of that reshaping.

There are many factors that determine the pressure profile between the eye and the contact lens. The shape of the wearer's eye is one such factor. Other factors include the diameter of the lens, the material from which the lens is made, the physical parameters relating to the material such as the elastic modulus, the thickness profile of the lens, and the shape of the posterior and anterior surfaces of the lens which also govern the thickness profile. In addition, a lens which is everted (that is, inside-out) will have internal stresses which will alter the pressure profile on the eye.

It will be appreciated that for effective reshaping of the surface of the eye a relatively high degree of predictability with respect to the pressure profile is important.

Applicant has developed a finite element model of the geometry and performance of soft contact lenses in order to provide the necessary degree of productivity for selecting a particular lens configuration for a specific wearer. A brief introduction to finite element analysis at this point may be of assistance to those readers less familiar with finite element techniques, which will then make the subsequent paragraphs relating to pressure profile prediction more readily understandable.

Finite element analysis (FEA) is the name given to a broad approach to the solution of physical problems in mechanics, dynamics, fluid dynamics and other fields. In general, problems that are analytically intractable, or impractical due to size or complexity, are candidates for finite element analysis. Solutions are generated numerically, usually by computer, and are stated to some known and acceptable degree of precision. A detailed description of the principles, techniques and practice of FEA may be found in, for example, Belytschko, Liu and Moran, *Nonlinear Finite Elements for Continua and Structures*, Wiley, 2001, among many other references.

The physical problem to be addressed is in several parts. Firstly, the problem of determining the pressure felt by the eye when a contact lens of a specified shape and material is pressed against the eye by a specified pressure. Secondly, the problem of determining the shape and internal state (stress, strain etc.) of the contact lens subjected to this pressure and constrained in its motion by the surface of the eye. Thirdly, the problem of determining the shape and internal state of a lens that has been everted. It will be appreciated by a person skilled in the art that each of these problems is able to be addressed by FEA, and that several equivalent approaches are possible. It will also be appreciated that the physical problems described above may be solved by methods other than FEA, and that all valid methods will provide results that are similar to a reasonable degree.

Figure 27:
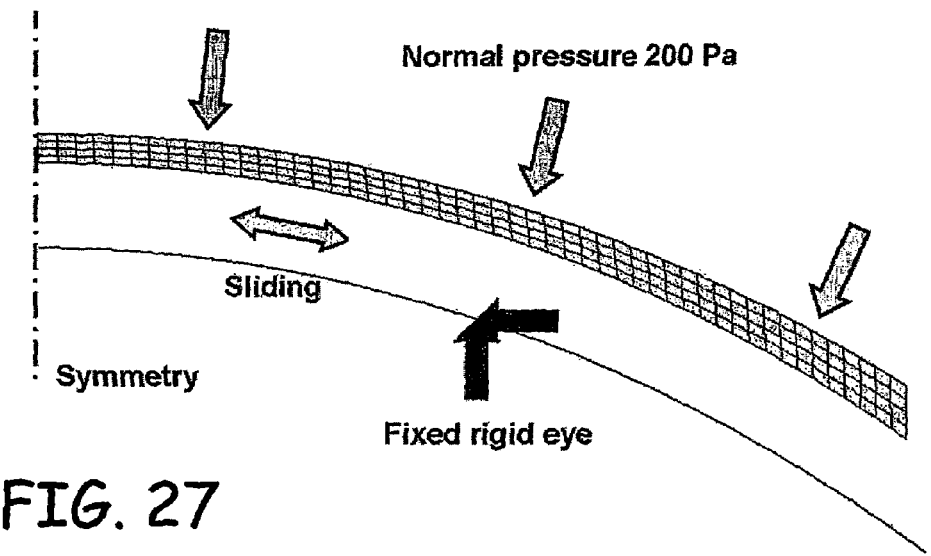
FIG. 27 shows diagrammatically a finite element model of a soft contact lens.

FIG. 27 presents a diagrammatic view of a finite element model of a soft contact lens. The lens is rotationally symmetric, so that only a half-cross-section need be modeled. The axis of symmetry lies to the left. The lens is decomposed into finite elements which behave as conceptual hoops, i.e. having annular shape about the axis of symmetry. Each element is given the properties of the material it is intended to mimic—in this case, a simple elastic material of specified Young's modulus, density and Poisson's ratio. The surface of the eye is modeled as a one-dimensional domain of rigid "contact" elements. When the lens is pressed against the eye by imposing a constant "eyelid" pressure on the surface of each element lying on its anterior surface, the contact elements model the pressure and sliding between the lens and eye. The lens will experience stresses and strains, will bend etc. in a realistic fashion.

Modeling Procedure

The model first generates a test lens geometry based on supplied parameters. In a two-step process, the model first everts the lens, and secondly applies a uniform pressure on the anterior surface in order to press the lens against an eye of specified shape. At each step the program records the shape of the lens and its internal stresses. After the final step, the program records the pressure transmitted to the eye, the lens-eye gap, and other parameters. Everted lens shapes may be analyzed by, for example, fitting conics to estimate central curvature.

Experimental Cases

The test cases (Table 4) were designed to cover a reasonable range of powers, and a range of elastic moduli spanning those of currently used soft contact lens materials.

TABLE 4

Schema of test cases, covering a back vertex power (BVP) range of +10 to −35 diopters, and a modulus range of 0.2 to 10.0 MPa for one representative power. Test cases are enumerated in the shaded boxes.

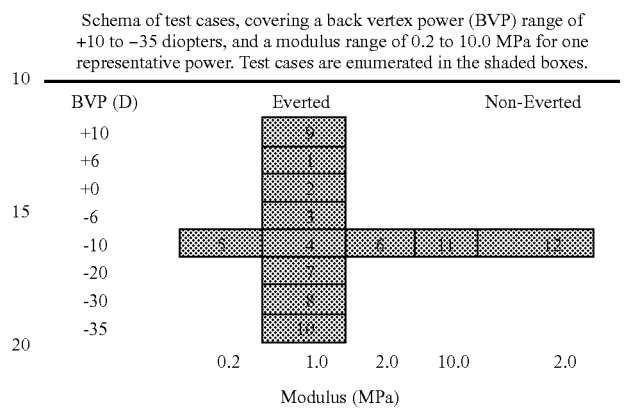

Test Lens Geometry and Material

Figure 28:
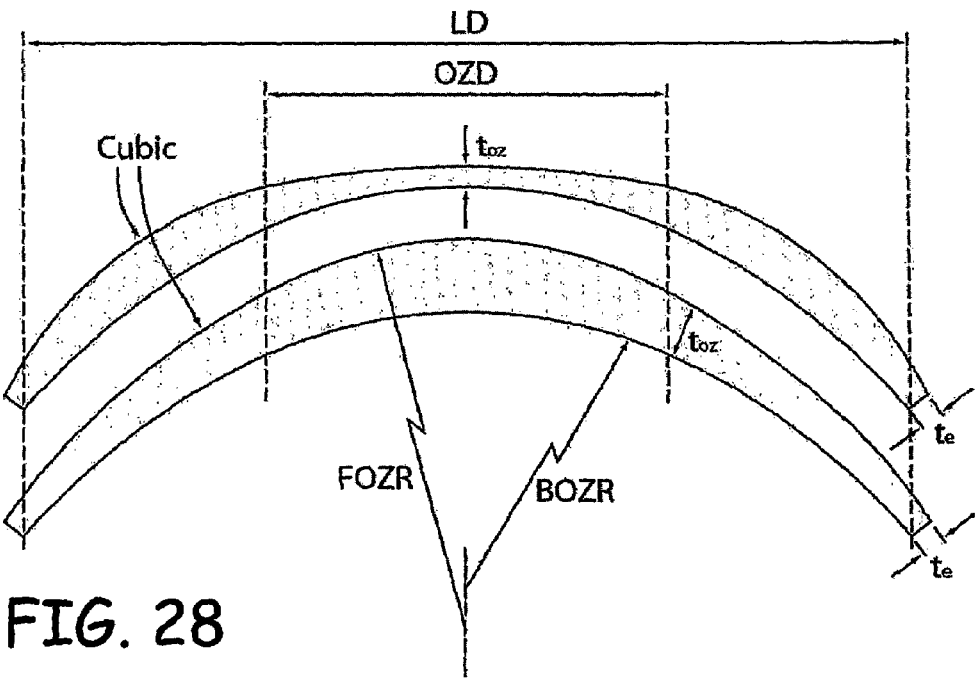
FIG. 28 depicts diagrammatically the geometric parameters of a typical soft lens.

The geometry of the test lenses was designed to be as simple as possible while remaining realistic, in order to minimize the effect of multiple geometric parameters. With this in mind, a spherical, monocurve geometry was chosen. As many design parameters as possible were fixed across all design variations. The lens substance was modeled as a simple linear elastic material. Design parameters were the back vertex power BVP, modulus of elasticity, back curve radius BOZR, minimum optic zone thickness $t_{oz}$, edge truncation thickness $t_e$, optic zone diameter OZD, lens diameter LD, and index of refraction n. The values of these parameters are shown in Table 5. The minimum optic zone thickness, $t_{oz}$, is applied at either the center of the lens or at the optic zone margin, depending on lens power (FIG. 28). The spherical front optic zone radius FOZR was calculated via the thick-lens paraxial equation in order to give the stated back vertex power for the given values of BOZR, n and $t_{oz}$. The front peripheral curve joining the optic zone margin to the edge truncation is a cubic polynomial having continuous slope at the optic zone margin, and peripheral edge slope matched to that of the back surface. The edge truncation is made normal to the back surface, and is of specified thickness $t_e$. FIG. 28 depicts diagrammatically the geometric parameters mentioned above. In addition to the elastic modulus, the contact lens material was also given a specified density and Poisson's ratio (1050 kg·m$^{-3}$ and 0.3 respectively). These values are within the range of current soft contact lens materials. Results are insensitive to the particular values chosen.

TABLE 5

Basic lens design parameters. As many parameters as possible are kept constant across all design variations. Optic zone diameter and minimum optic zone thickness are changed for cases 7 to 10 in order to limit overall thickness to realistic values. Refractive index of lens material is 1.42 throughout.

| Case | BVP (D) | Modulus (MPa) | Everted | LD (mm) | BOZR (mm) | $t_e$ (mm) | OZD (mm) | $t_{oz}$ (mm) |
|---|---|---|---|---|---|---|---|---|
| 9 | +10 | 1.0 | Yes | All | All | All | 6.00 | 0.20 |
| 1 | +6 | 1.0 | Yes | 13.8 | 8.60 | 0.08 | 8.00 | 0.08 |
| 2 | +0 | 1.0 | Yes | | | | | |
| 3 | −6 | 1.0 | Yes | | | | | |
| 4 | −10 | 1.0 | Yes | | | | | |

TABLE 5-continued

Basic lens design parameters. As many parameters as possible are kept constant across all design variations. Optic zone diameter and minimum optic zone thickness are changed for cases 7 to 10 in order to limit overall thickness to realistic values. Refractive index of lens material is 1.42 throughout.

| Case | BVP (D) | Modulus (MPa) | Everted | LD (mm) | BOZR (mm) | $t_e$ (mm) | OZD (mm) | $t_{oz}$ (mm) |
|---|---|---|---|---|---|---|---|---|
| 12 | −10 | 1.0 | No | | | | | |
| 5 | −10 | 0.2 | Yes | | | | | |
| 6 | −10 | 2.0 | Yes | | | | | |
| 11 | −10 | 10.0 | Yes | | | | | |
| 7 | −20 | 1.0 | Yes | | | | 6.00 | 0.04 |
| 8 | −30 | 1.0 | Yes | | | | | |
| 10 | −35 | 1.0 | Yes | | | | | |

Eversion Step and Everted Geometry Results

The test lenses were first everted in the absence of the eye. Since the lens material is assumed to be purely elastic, the order of loading is unimportant. To evert the lens, the edge was first constrained in the axial direction. The back surface was then subjected to a forced displacement sufficient to bring the lens into an approximately everted shape. Lastly, the lens was allowed to relax into its final everted shape by fixing the central point of the (new, resultant) back surface in space and removing all constraints. At each stage in the modeling process, points on the axis of symmetry were constrained to have no motion normal to the axis. The relationship between the everted and non-everted geometry of each test lens is shown in Table 6. Since the everted geometry depends on the relative stresses between different parts of the lens (not on absolute stresses), we expect that two lenses with identical geometry but different moduli will have identical everted shapes. This expectation is borne out in the results of Table 6. Note also that it is possible to construct a lens having no stable everted shape, or an everted shape having stability characteristics such that it may be difficult to attain or maintain the eversion.

Figure 29:
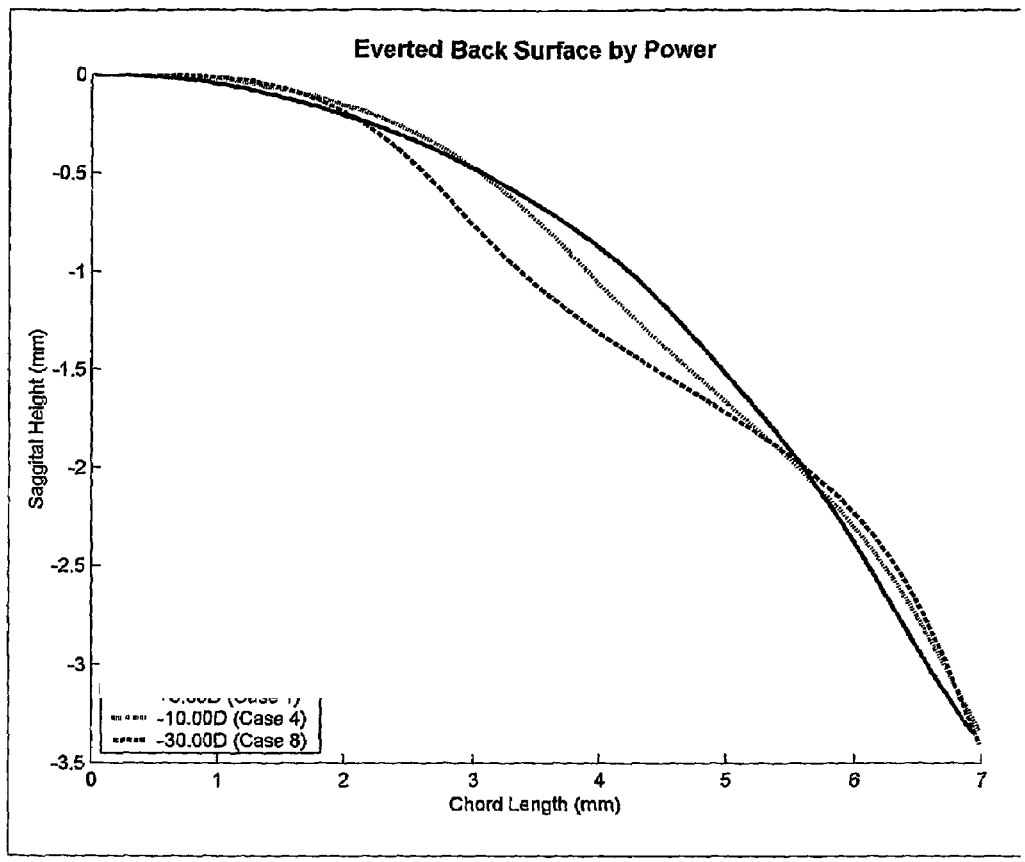
FIG. 29 shows diagrammatically the everted posterior surface of three different lenses.
Figure 30:
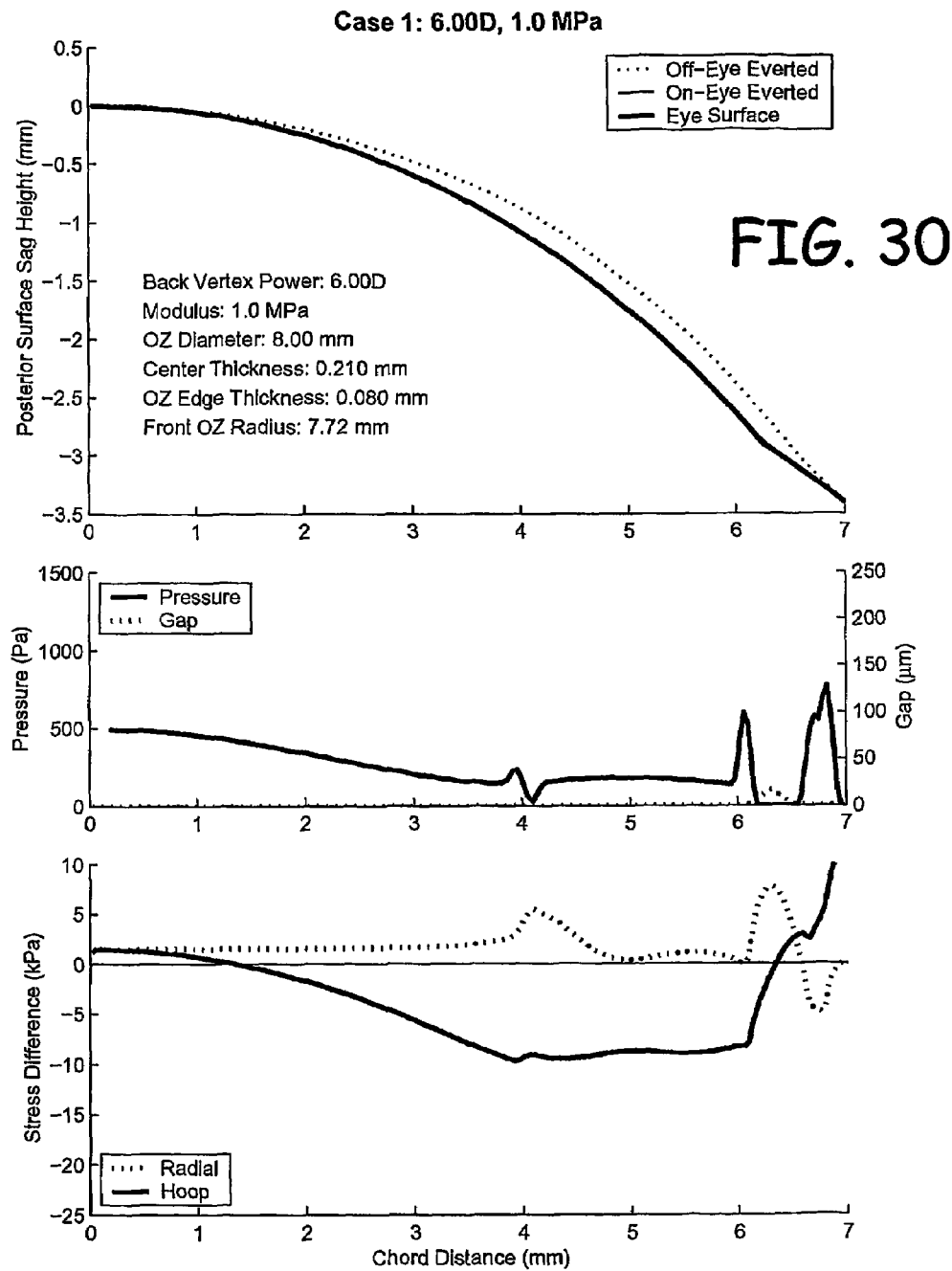
FIGS. 30 to 41 show surface sag, gap (i.e. tear thickness), pressure and stress differential plots of twelve different lenses modeled in accordance with the invention.
Figure 31:
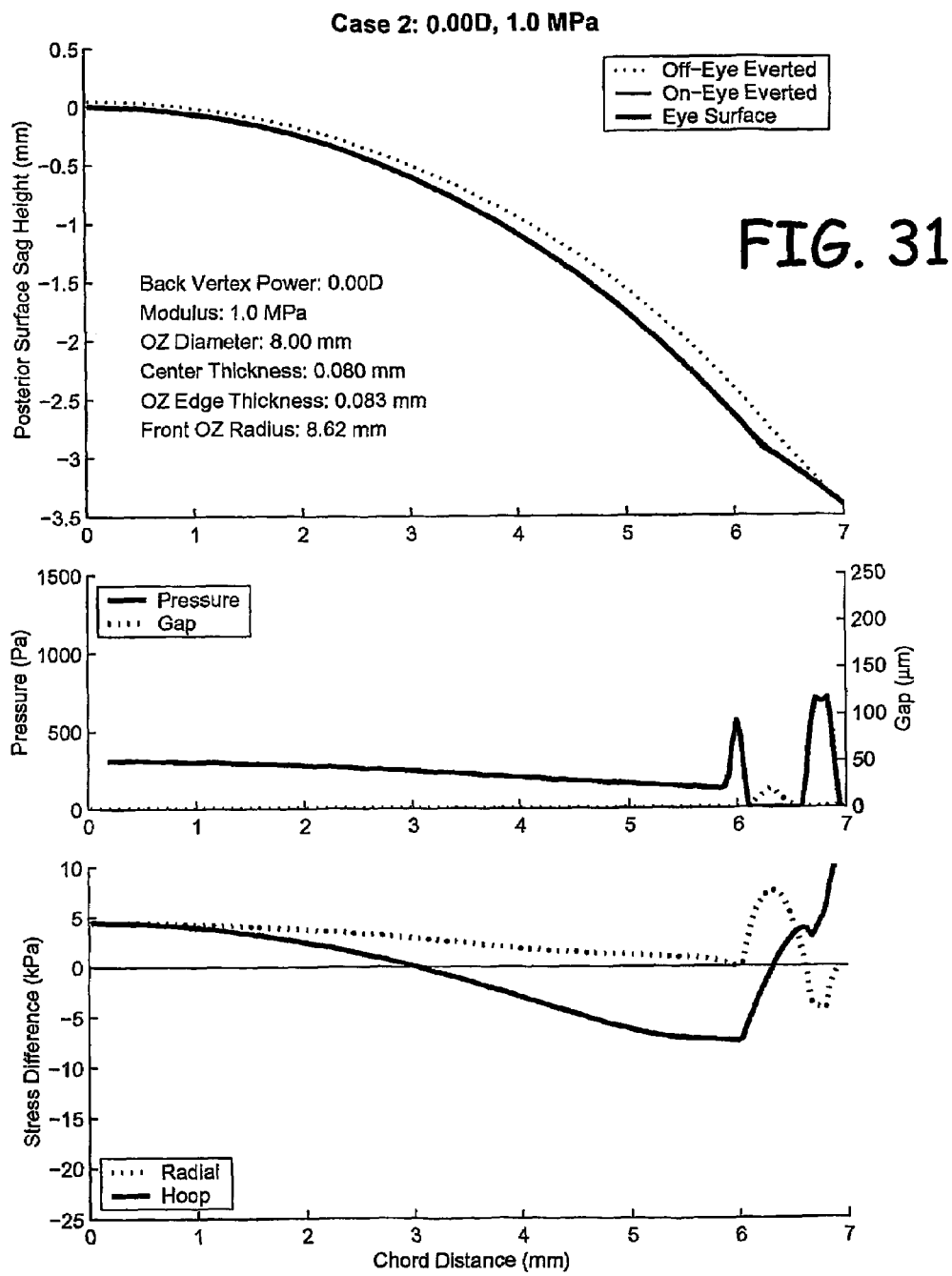
Figure 32:
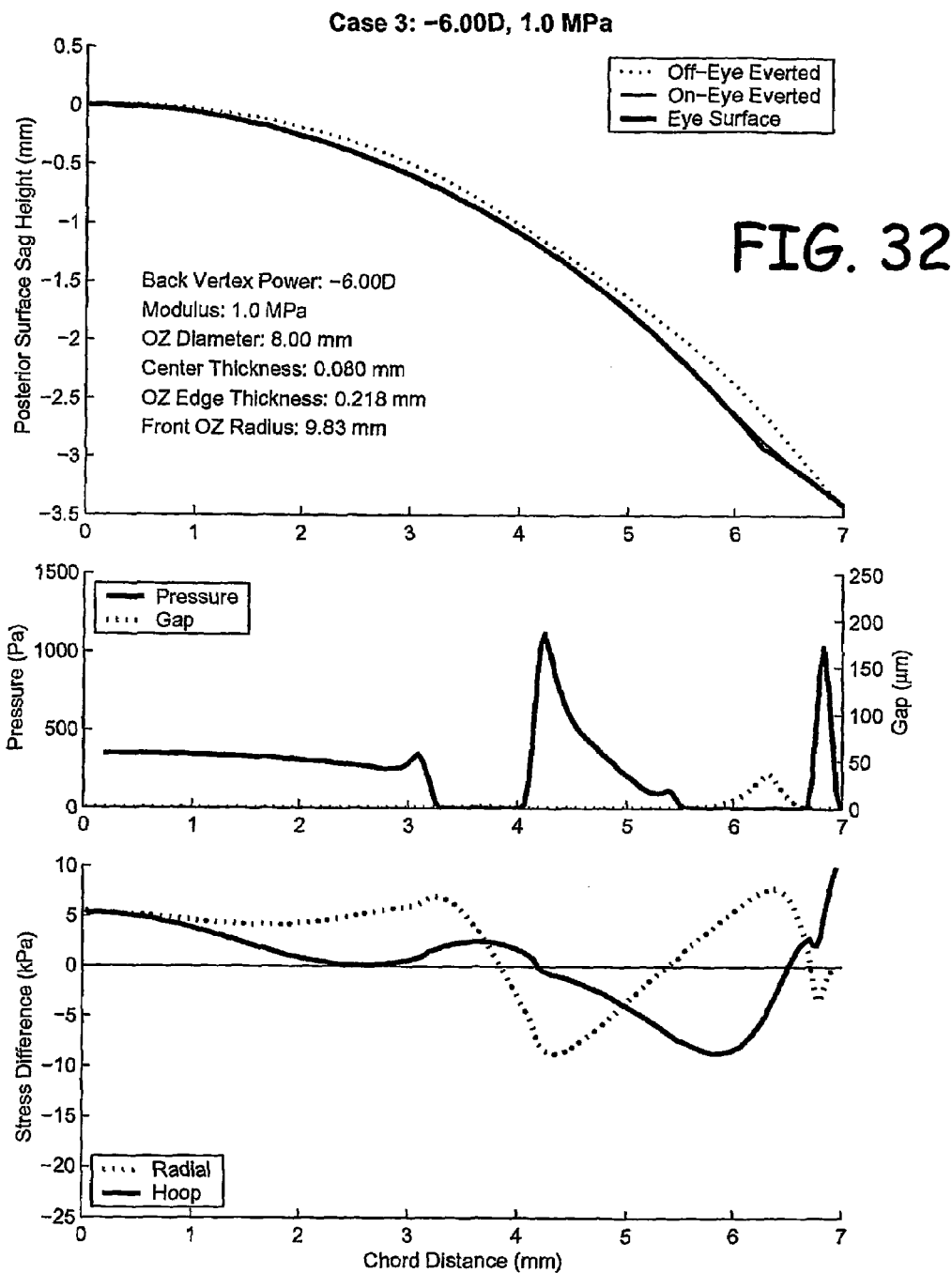
Figure 33:
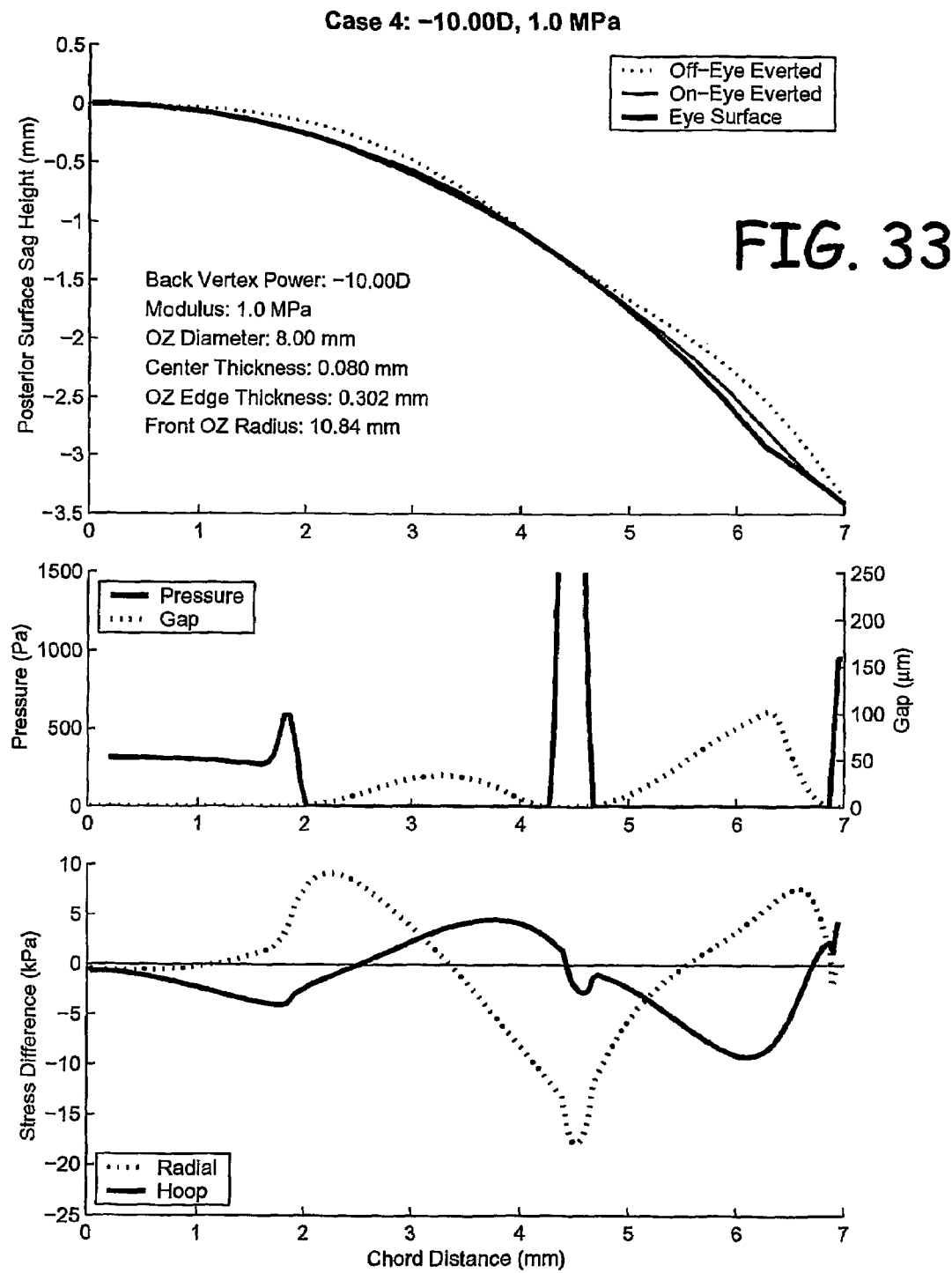
Figure 34:
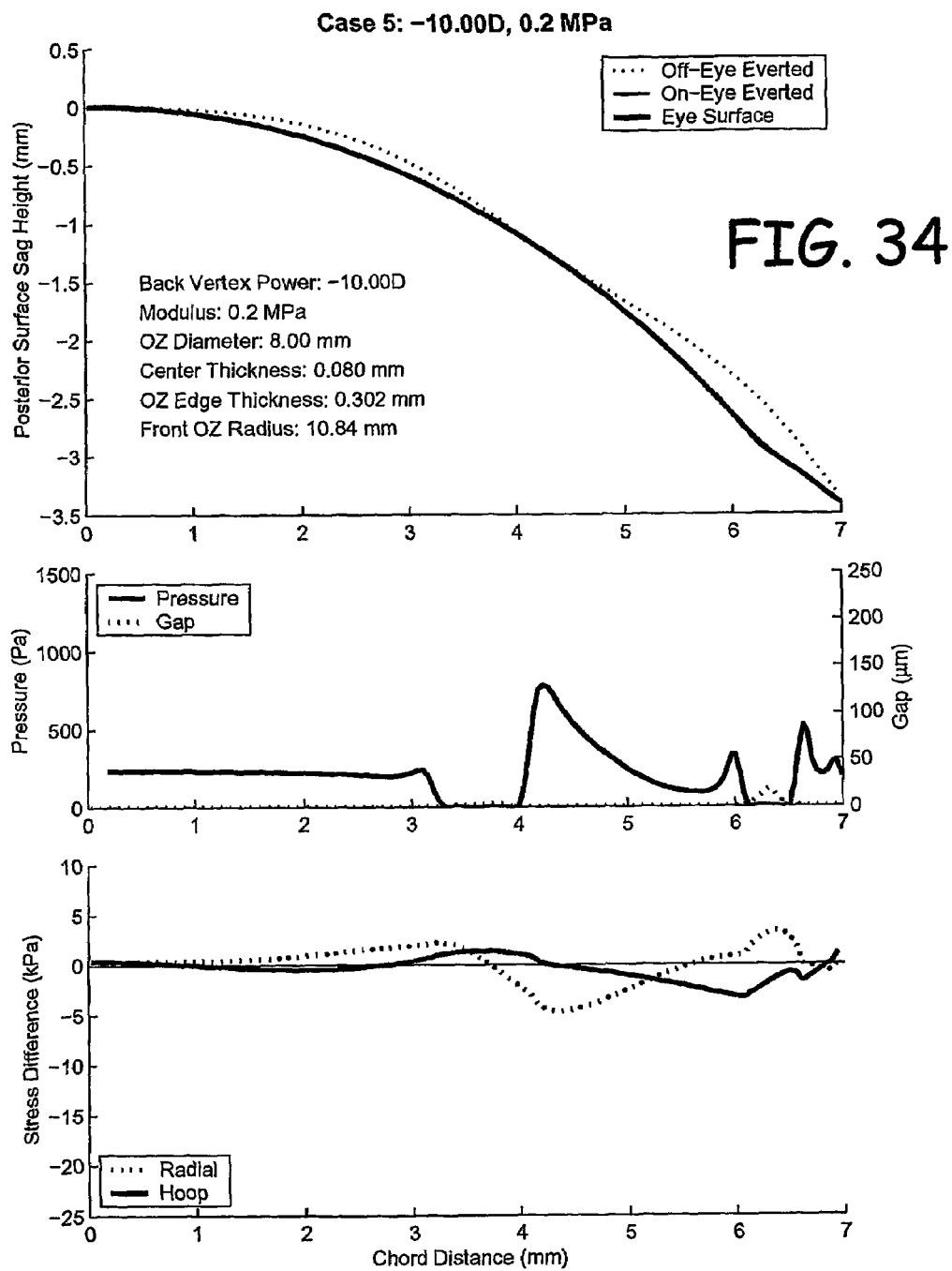
Figure 35:
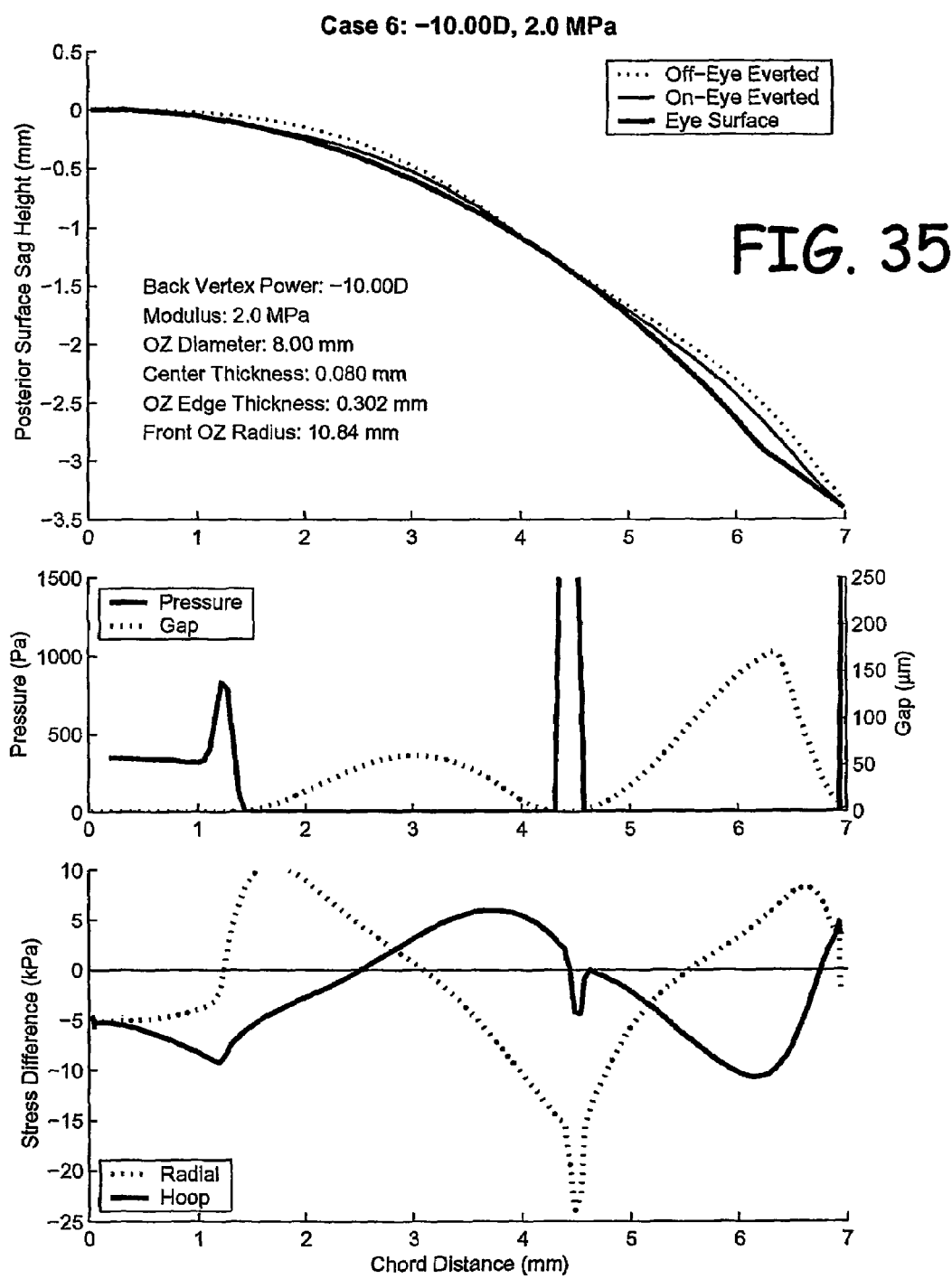
Figure 36:
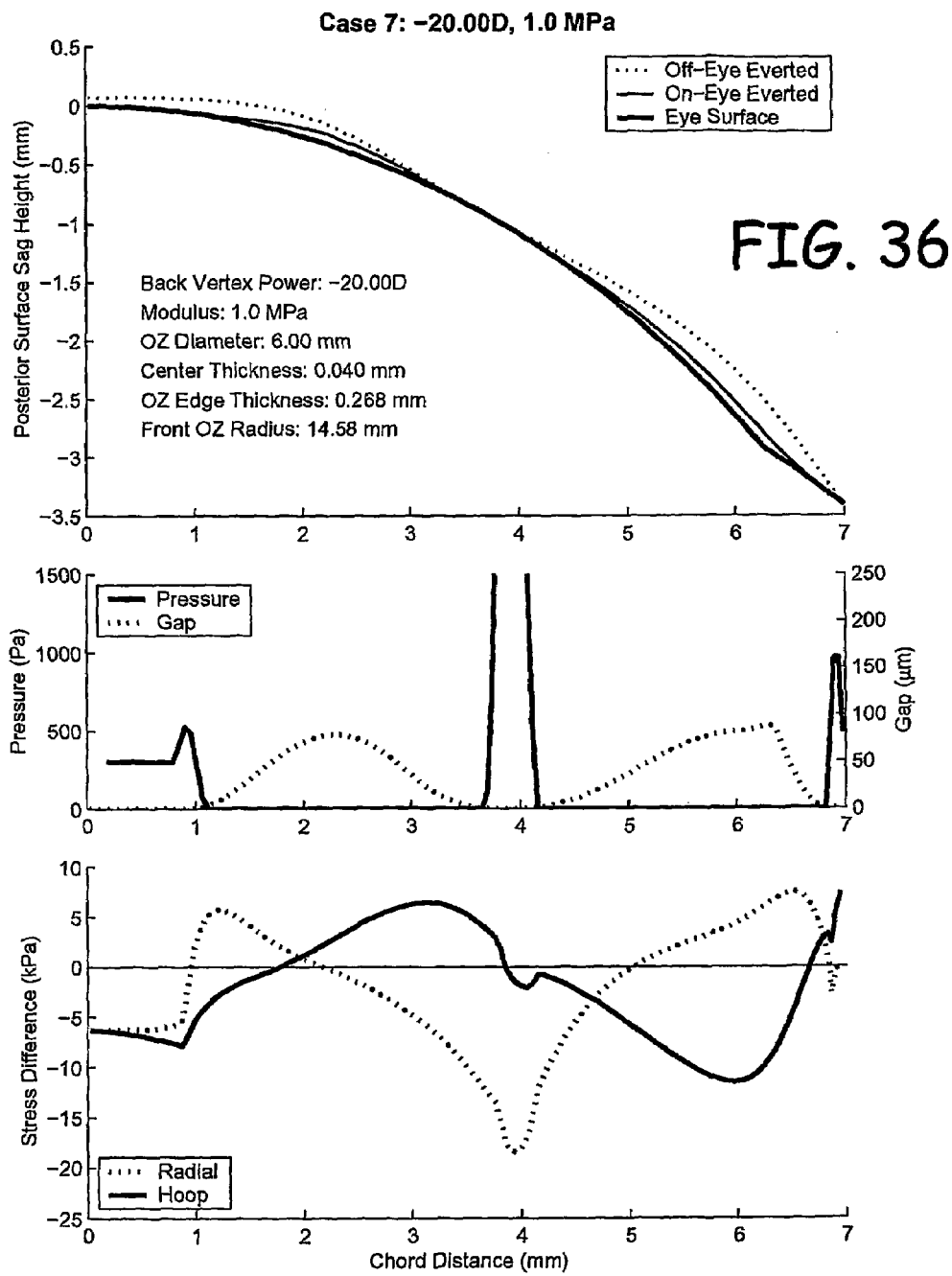
Figure 37:
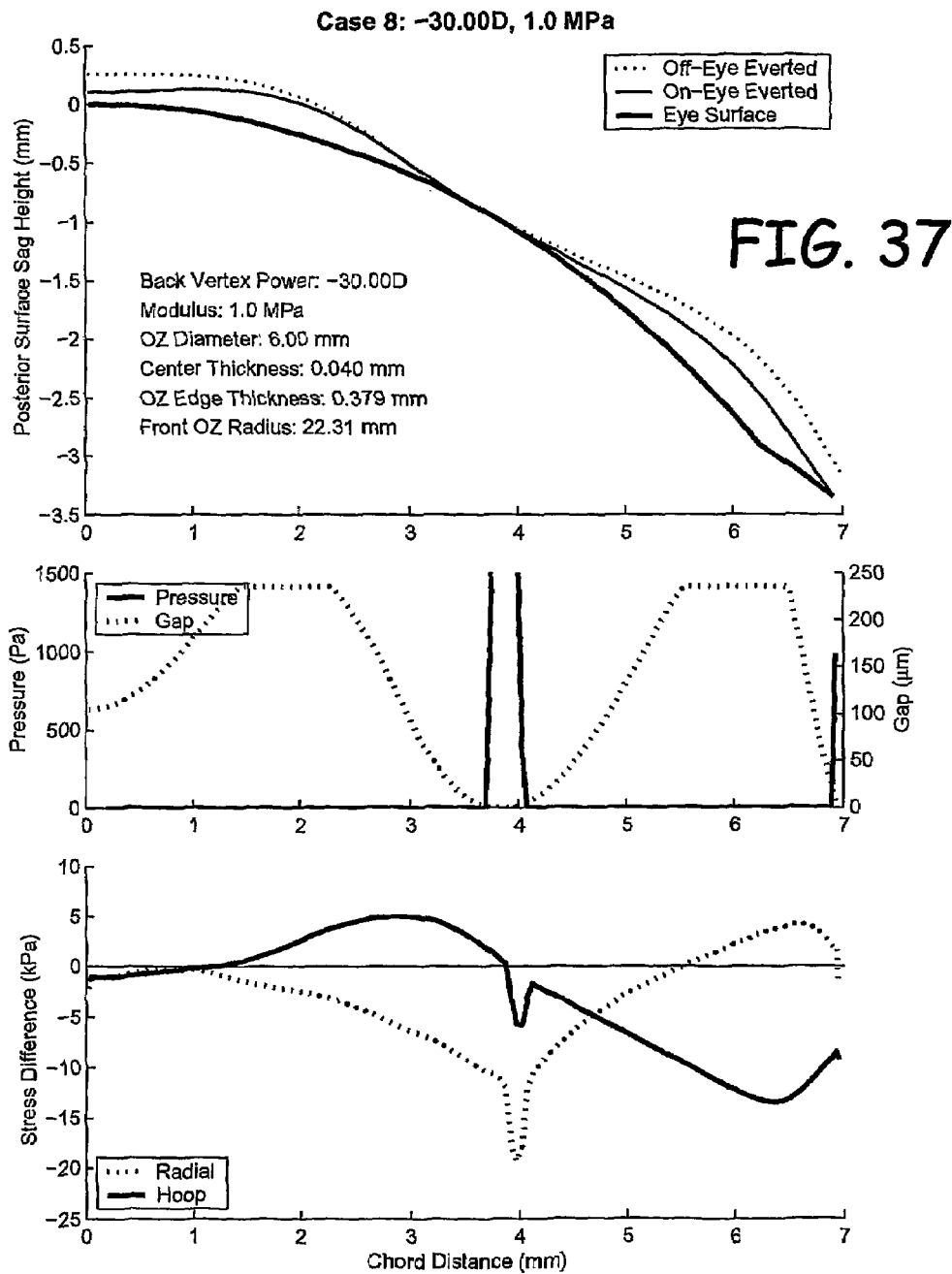
Figure 38:
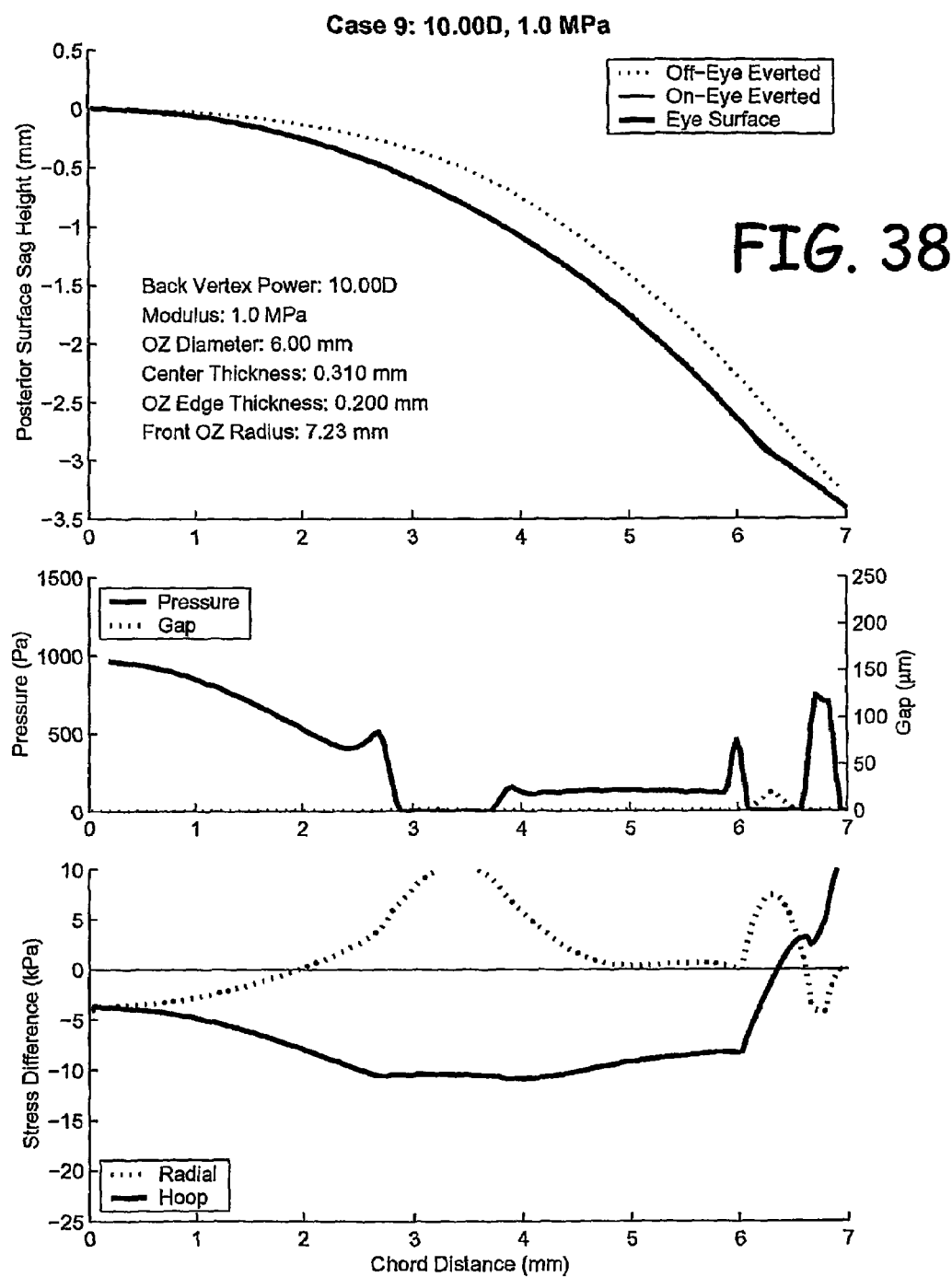
Figure 39:
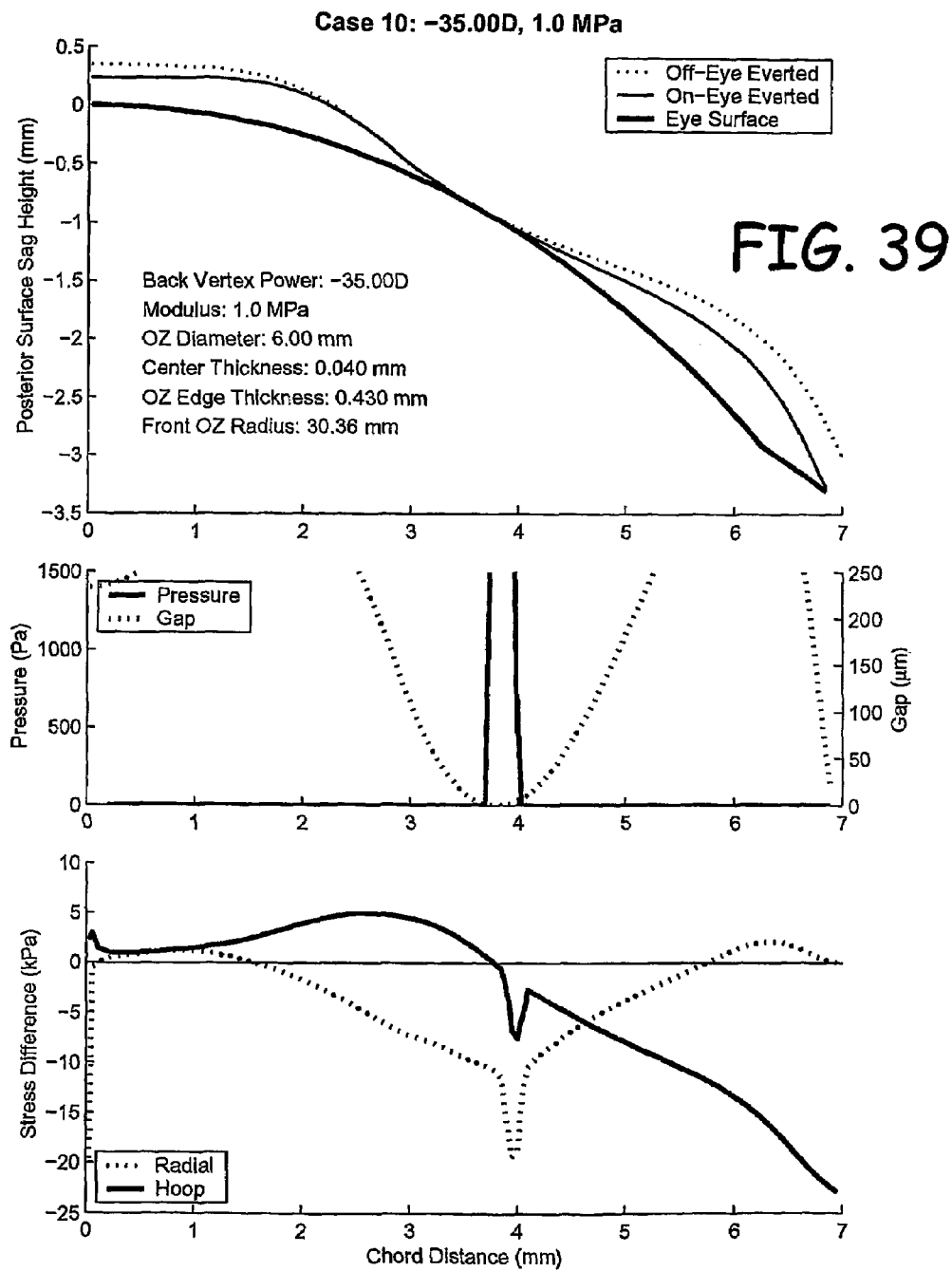
Figure 40:
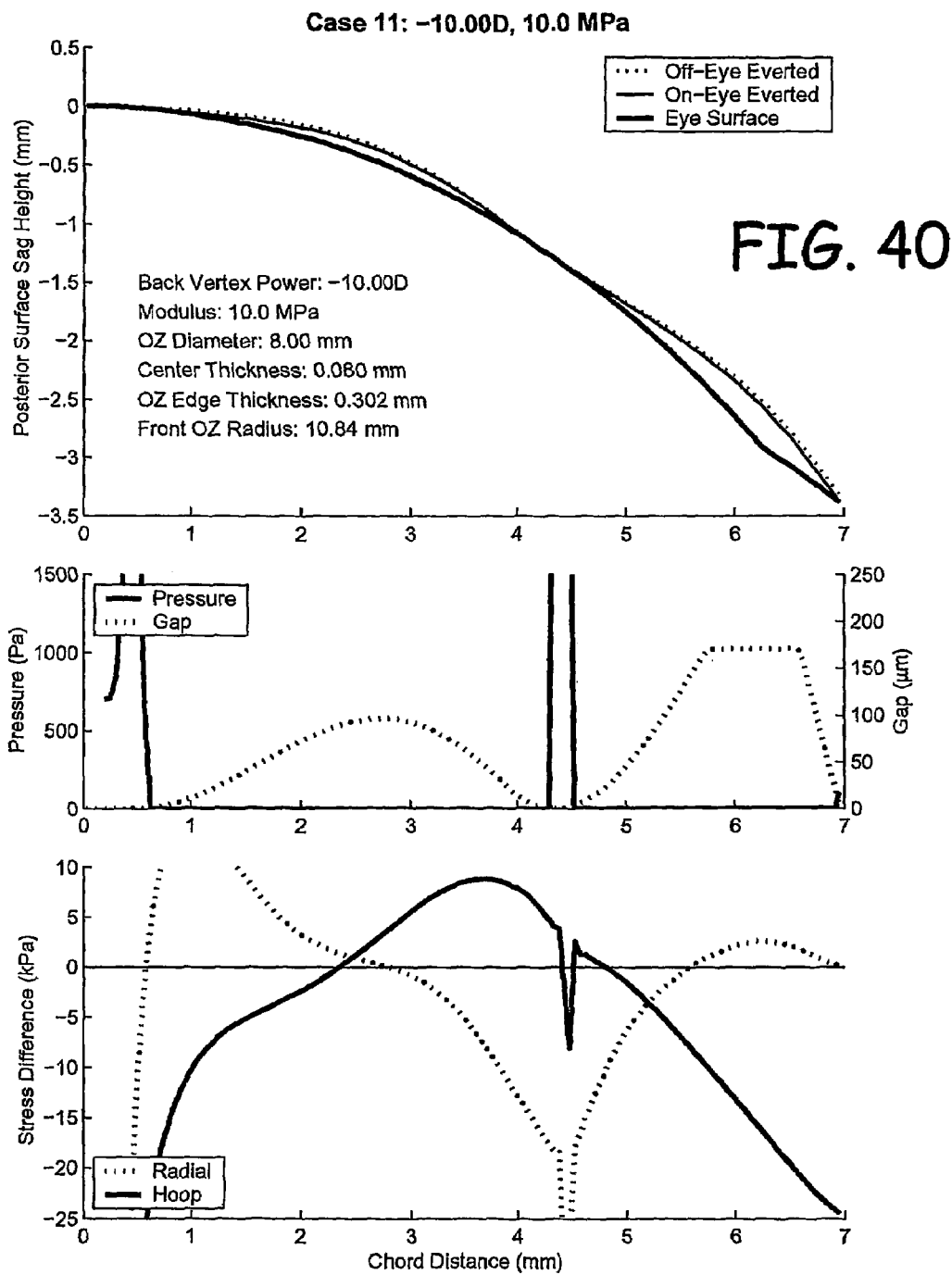

FIG. 29 shows the everted back surface shapes of representative plus-powered (case 1), minus-powered (case 4) and high-minus-powered (case 8) lenses. The evolution of a "staircase" back surface shape with increasingly negative power is apparent. This staircase shape divides the lens into annular regions of different gap and pressure characteristics.

TABLE 6

Change in back surface diameter and sag height of the everted test lenses. Original diameter and sag for all lenses were 13.8 mm and 3.47 mm respectively. All lenses became wider and flatter when everted. Other parameters being equal, modulus has no effect on everted geometry (cases 4-6). Minus-powered lenses adopt a "staircase" back surface shape when everted (see FIG. 29).

| Case | Power (D) | Modulus (MPa) | Diameter (mm) | ΔDiameter (mm) | Sag (mm) | ΔSag (mm) |
|---|---|---|---|---|---|---|
| 9 | +10 | 1.0 | 13.91 | 0.11 | 3.47 | −0.22 |
| 1 | +6 | 1.0 | 13.90 | 0.10 | 3.36 | −0.10 |
| 2 | +0 | 1.0 | 13.91 | 0.11 | 3.43 | −0.04 |
| 3 | −6 | 1.0 | 13.94 | 0.14 | 3.40 | −0.06 |
| 4 | −10 | 1.0 | 13.99 | 0.19 | 3.35 | −0.11 |
| 5 | −10 | 0.2 | 13.99 | 0.19 | 3.35 | −0.11 |
| 6 | −10 | 2.0 | 13.99 | 0.19 | 3.35 | −0.11 |
| 11 | −10 | 10.0 | 13.99 | 0.19 | 3.35 | −0.11 |
| 7 | −20 | 1.0 | 13.93 | 0.13 | 3.43 | −0.04 |
| 8 | −30 | 1.0 | 13.99 | 0.19 | 3.42 | −0.04 |
| 10 | −35 | 1.0 | 14.04 | 0.24 | 3.38 | −0.09 |

Model Eye

Closed-eye pressure profiles are simulated by the introduction of a solid cornea and section of sclera. The eye shape profile is assumed to be rotationally symmetric, and has geometric parameters considered to be representative of the population average. In particular, central corneal radius $r_0$=7.8 mm, corneal diameter CD=12.5 mm, corneal p-value p=0.75, and scleral radius SR=12.0 mm.

Pressure Step and On-Eye Pressure Results

After eversion, an inflexible model eye is introduced. A more advanced version of the model, however, may include a flexible or malleable eye. The model eye is constrained to have no translational or rotational motion. All constraints are removed from the model contact lens, except those required by symmetry, and an external force consisting of a constant normal pressure on the anterior surface of the lens is imposed. The pressure exerted by the closed eyelid is estimated to be in the range of 100-300 Pa; here a pressure of 200 Pa is used. The finite element contact algorithm is activated in this phase of the analysis. For contact analysis, the anterior surface of the lens is overlaid with "contact" elements, and the surface of the eye is overlaid with "target" elements. These two element types detect mutual proximity and contact, and, when contact between the two surfaces is established, simulate the proper physics of sliding, pressure etc. between them. Upon the imposition of the pressure force, the model is run to static equilibrium. The everted contact lens is thus pressed onto the model eye, and its shape change, internal stress state, contact pressure and the like are recorded.

The final results for the eleven everted lens test cases are summarized in FIGS. 30-41. In each figure, the top panel shows the back surface of the everted lens in the "just touching" or off-eye configuration, before pressure is applied, and also in the equilibrium on-eye configuration after pressure is applied. The flexure of the everted lens by the eyelid is thus visible. When the eyelid is opened, the lens will tend to return to its everted "just touching" configuration. Thus, the plot helps to visualize the "sucking" or "pumping" action of the lens as the wearer blinks.

The middle panel shows the pressure felt by the eye, and the gap between the eye and lens. The scale is identical across all the figures, so that they are directly comparable.

The lower panel shows back surface stress difference within the contact lens, i.e. (closed-eye stress)-(open-eye stress). A negative value indicates that the stress became more compressive when the eyelid pressure was applied. In general, making the lens steeper (increasing its curvature) in some region will give compressive hoop stress. The stress difference is useful to picture how out-of-equilibrium the lens becomes, after being subjected to eyelid pressure.

Figure 41:
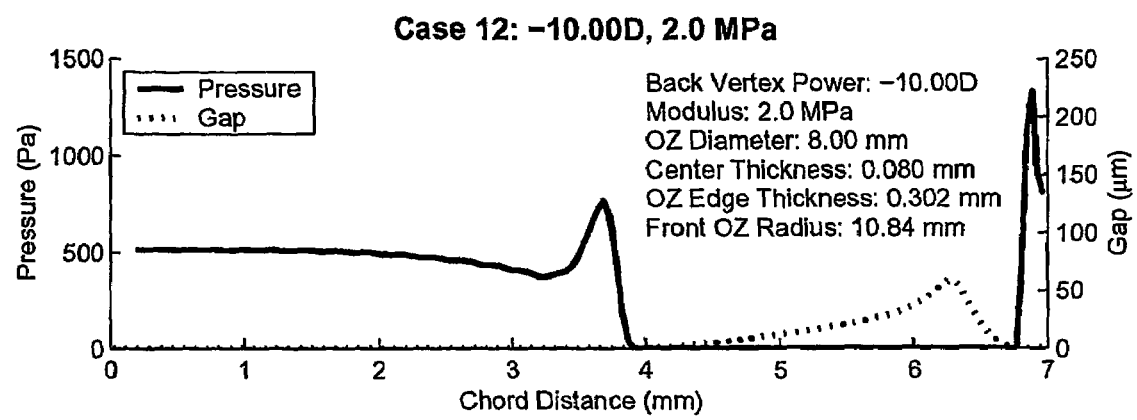

In case 12, a non-everted −10D contact lens with a modulus of 2.0 MPa is pressed onto the eye. The resultant pressure and gap profiles are shown in FIG. 41. The mean pressure in an annular zone approximately 3.25-3.80 mm from the center of the lens is higher than the mean pressure in the annular zone approximately 0-3.25 mm from the center. In addition, for this case, an additional annular zone of lower pressure exists approximately 3.80-6.80 mm from the center of the lens. This overall pressure profile will, it is anticipated, result in a redistribution of corneal thickness away from the zone of higher pressure. Due to the small gaps and relatively low gradients in pressure that exist under this contact lens, it is expected that this contact lens will have a only small corneal reshaping effect. However, it should be noted that pressure gradients suitable for corneal reshaping could be achieved through non-everted soft lenses albeit its efficacy may be below those of everted lenses.

Lens Design Process

There are several ways in which the current model may be used to design a soft contact lens which, when everted, will produce predictable pressure and gap profiles, and hence a predictable orthokeratology effect. The clinical results described elsewhere in this document form a reference set by which the orthokeratology effect of a number of particular lens designs is known. The clinical results therefore embody a series of connections between known outcomes and particular lens designs.

The model may be applied iteratively in order to interpolate or extrapolate the known designs associated with known outcomes. For example, the experimenter may start with measurements of a patient's corneal shape and refractive error, and hence the required outcome. The lens design process then begins with the known lens design that is understood, from clinical results, to produce an outcome closest to the desired outcome. The gap profile, for instance, may then be adjusted by the experimenter by adjusting the non-everted front surface shape of the lens. Each iteration may be tested by running the model. The pressure profile may then be adjusted by similar experimentation with lens thickness, and modulus if appropriate. In this way the experimenter can arrive at an acceptable orthokeratology outcome over the course of several model runs. To produce a usable contact lens, the experimenter would then adjust the optical zone in order to deliver acceptable visual performance, then adjust the edge shape and other finer details. The lens may then be fabricated. Each successful design, having been tested on-eye and its clinical outcome determined, becomes a part of the original knowledge set, thus accelerating the process for the next design.

More efficient improvements on the basic method described above can be devised. Many of these methods involve some kind of state-space model for reaching a solution. In one variation, a "response surface" is constructed by deriving approximations to the derivatives of the model outcome parameters with respect to the input design parameters. From knowledge of the model results at a number of locations in input-parameter space, an approximate response surface may be constructed using interpolating functions such as Taylor series. The response surface provides information about how the model results will change in response to a specified change in one or more input design parameters. The experimenter may use this state-space model to rapidly "zoom in" on a particular design solution. In addition, such an approach may be made part of the model, so that the search for acceptable solutions becomes at least semi-automated. The response surface method described here is one of a broad family of extensions to the basic method, known variously as "function minimization", "multidimensional minimization", "optimization", "extremum search methods", and other names that will be recognized by those skilled in the art.

The methods described above may be used to develop contact lens designs on a custom basis. By measuring a single patient's corneal shape and refractive error, and proceeding as described, a lens specific for that patient may be designed and fabricated.

The methods described above may be used to develop designs (stock control units) for specific groups of patients. By accumulated experience, or by an analysis of the sensitivity of outcomes to various design parameters, it will be apparent to the experimenter that such designs exist. To develop such designs, the experimenter may take a specific lens design, and run the model several times while varying the input parameters corresponding to patient details (corneal geometry etc.). The design in question may then be rated as to its performance in each case. The range of patients for which it is suitable may therefore be determined. In an alternative procedure, the experimenter may begin with a number of patients suspected or known to have similar outcomes in other orthokeratology treatment modalities (e.g. RGP), and iteratively design a lens having acceptable performance for all patients in the group. It will be appreciated that a combination of these two approaches is also possible.

Using the procedure described above, it will be possible to choose a range of lens designs, each meeting the needs of a certain patient group. To cater for the needs of a wide population of patients, it may therefore be needful only to manufacture a much smaller number of contact lens designs (stock control units). Such stock control units may be mass-produced for wide distribution using current lens molding technology, for example.

Variations may be made to the methodologies described above without departing from the scope of the invention. In particular, the finite element model (or other pressure estimation model) may vary from that described herein.

However, a combination of mathematical modeling and clinical observations will enable the design of precisely shaped soft contact lenses for precision corneal reshaping.

The invention claimed is:

1. A soft contact lens having a diameter of greater than the limbal diameter and formed of a homogenous material having an elastic modulus between 0.2 and 10 MPa, said lens having a generally concave posterior surface for fitting to the eye of a wearer, and a convex anterior surface, the contact lens having mechanical properties and/or a geometric shape such that when the lens is fitted to the eye the pressure applied to the eye by or via the lens will vary in a radial direction between at least one zone of higher pressure and at least one zone of lower pressure, the pressure gradient between said zones, and the location of said zones, being selected so as to cause a dimensional change to the surface layer of the cornea of the eye to thereby at least temporarily cause the refractive state of the eye to change.

2. A soft contact lens according to claim 1 wherein said posterior surface has a shape that differs from the contour of the eye such that a first annular portion of the lens at a selected radial distance from the center of the lens will be closer to the surface of the eye than a second annular portion of the lens at a different second selected radial distance from the center of the lens.

3. A soft contact lens according to claim 2 wherein the pressures applied to the eye at the first annular portion and at the second annular portion are such as to define a pressure gradient which is sufficiently steep that epithelial thickness will tend to increase from the zone of high pressure towards the zone of low pressure.

4. A soft contact lens according to claim 1 wherein the lens is constructed so as to have a natural orientation and an evened orientation and is functional in both orientations, the lens being stable in the evened orientation when placed on the eye, and wherein the posterior surface of the lens in said evened orientation is defined by the anterior surface of the lens in said natural orientation.

5. A soft contact lens according to claim 1 wherein the lens is formed of a material with oxygen transmissibility greater than 87 barrers.

6. A soft contact lens according to claim 1 wherein the lens is comprised of a silicone hydrogel material.

7. A soft contact lens according to claim 1 wherein the lens has a back vertex power of between +10D and −35D.

8. A soft contact lens according to claim 1 wherein the lens has a center thickness of between 0.04 mm and 0.31 mm.

9. A soft contact lens according to claim 1 having an annular zone of lower pressure at a distance less than approximately 4 mm from the center of the lens.

10. A soft contact lens according to claim 1 having an annular zone of higher pressure at a distance of approximately between 3 mm and 6 mm from the center of the lens.

11. A method of refractive error reduction of an eye by corneal reshaping including:
   determining the required refractive correction for the eye;
   characterizing the surface shape of at least that part of the eye which is to be subjected to reshaping; and
   selecting a soft lens formed of a material and having a geometric configuration such that when fitted to the eye will apply pressures to the surface of the eye in such manner as to assist in the required corneal reshaping the selected lens being of a type that has been manufactured so as to have a natural orientation and an evened orientation and is functional in both orientations, said lens being stable in the everted orientation when placed on the eye.

12. A method according to claim 11 wherein said selection process involves a modeling process adapted to predict anticipated pressures and different zones of the wearer's eye.

13. A method according to claim 12 wherein said modeling process is a finite element modeling process.

* * * * *